US011684572B2

(12) United States Patent
Powell et al.

(10) Patent No.: US 11,684,572 B2
(45) Date of Patent: *Jun. 27, 2023

(54) METHODS FOR PRODUCING CARBOXYLATE LIGAND MODIFIED FERRIC IRON HYDROXIDE COLLOIDS AND RELATED COMPOSITIONS AND USES

(71) Applicant: United Kingdom Research and Innovation, Swindon (GB)

(72) Inventors: Jonathan Joseph Powell, Cambridge (GB); Nuno Jorge Rodrigues Faria, Milton Ernest (GB)

(73) Assignee: United Kingdom Research and Innovation, Swindon (GB)

( * ) Notice: Subject to any disclaimer, the term of this patent is extended or adjusted under 35 U.S.C. 154(b) by 69 days.

This patent is subject to a terminal disclaimer.

(21) Appl. No.: 16/747,821

(22) Filed: Jan. 21, 2020

(65) Prior Publication Data

US 2020/0155453 A1 May 21, 2020

Related U.S. Application Data

(63) Continuation of application No. 15/765,367, filed as application No. PCT/EP2016/074022 on Oct. 7, 2016, now Pat. No. 10,722,459.

(30) Foreign Application Priority Data

Oct. 9, 2015 (GB) ..................... 1517893

(51) Int. Cl.
    *A61K 9/00* (2006.01)
    *A23L 33/165* (2016.01)
    *A61K 31/295* (2006.01)
    *A61K 9/10* (2006.01)
    *A61K 33/26* (2006.01)
    *A61K 9/14* (2006.01)

(52) U.S. Cl.
CPC .......... *A61K 9/0095* (2013.01); *A23L 33/165* (2016.08); *A61K 9/10* (2013.01); *A61K 31/295* (2013.01); *A61K 33/26* (2013.01); *A23V 2002/00* (2013.01); *A61K 9/0053* (2013.01); *A61K 9/14* (2013.01)

(58) Field of Classification Search
None
See application file for complete search history.

(56) References Cited

U.S. PATENT DOCUMENTS

| | | | |
|---|---|---|---|
| 3,076,798 | A | 2/1963 | Mueller et al. |
| 3,821,192 | A | 6/1974 | Montgomery et al. |
| 7,943,664 | B2 | 5/2011 | Powell et al. |
| 8,058,462 | B2 | 11/2011 | Powell et al. |
| 2005/0256328 | A1 | 11/2005 | Justus et al. |
| 2006/0205691 | A1 | 9/2006 | Geisser et al. |
| 2008/0188555 | A1 | 8/2008 | Powell et al. |
| 2008/0274210 | A1 | 11/2008 | Chan et al. |
| 2010/0032374 | A1 | 2/2010 | Powell et al. |
| 2010/0217025 | A1 | 8/2010 | Kwok et al. |

FOREIGN PATENT DOCUMENTS

| | | |
|---|---|---|
| WO | 2003092674 A1 | 11/2003 |
| WO | 2003097627 A1 | 11/2003 |
| WO | 2004074444 A2 | 9/2004 |
| WO | 2005000210 A2 | 1/2005 |
| WO | 2004074444 A3 | 4/2005 |
| WO | 2005094203 A2 | 10/2005 |
| WO | 2006037449 A2 | 4/2006 |
| WO | 2008096130 A1 | 8/2008 |
| WO | 2015178451 A1 | 11/2015 |

OTHER PUBLICATIONS

Aslam et al., "Ferroportin mediates the intestinal absorption of iron from a nanoparticulate ferritin core mimetic in mice," The FASEB Journal, vol. 28, pp. 3671-3678, Aug. 2014.
Bobtelsky et al., "The Structure and Behavior of Ferric Tartrate and Citrate Complexes in Dilute Solutions," J. Am. Chem. Soc. 69(10):2268-2290, Oct. 1947. Presented at the 110th Meeting of the American Chemical Society, Chicago, Sep. 1946.
Geisser et al., "Pharmacokinetics of Iron Salts and Ferric Hydroxide-Carbohydrate Complexes," Drug Res. 37(1):100-104, 1987.
Harvey et al., "Ferric trimaltol corrects iron deficiency anaemia in patients intolerant of iron," Aliment. Pharmacol. Ther. 12:845-848, 1998.
Heinrich, "Bioavailability of Trivalent Iron in Oral Iron Preparations," Arzneim-Forsch. (Drug Res.) 25(3):420-426, 1975.
Nielsen et al., "Bioavailability of Iron from Oral Ferric Polymaltose in Humans," Arzneim-Forsch (Drug Res.) 44(1):743-748, 1994.
Pereira et al., "Nanoparticulate iron(III) oxo-hydroxide delivers safe iron that is well absorbed and utilised in humans," Nanomedicine 10(8):1877-1886, 2014.
Powell et al., "A nano-disperse ferritin-core mimetic that efficiently corrects anemia without luminal iron redox activity," Nanomedicine 10(7):4529-1538, 2014.
Rose et al., 2002, "Synthesis and Characterization of Carboxylate-FeOOH Nanoparticles (Ferroxanes) and Ferroxane-Derived Ceramics," Chem. Mater. 14: 621-628.
International Search Report and Written Opinion issued in International Application No. PCT/EP2016/074022, dated Dec. 13, 2016, 12 pages.

(Continued)

*Primary Examiner* — Katherine Peebles
(74) *Attorney, Agent, or Firm* — McNeill Baur PLLC

(57) ABSTRACT

Processes for recovering colloids of carboxylate ligand modified ferric iron hydroxide materials such as IHAT (Iron Hydroxide Adipate Tartrate) are described based on the use of water miscible non-aqueous solvents, such as ethanol, methanol and acetone. The processes produce materials with advantageous properties such as improved bioavailability, reduced aggregation and/or agglomeration and/or increased iron content.

30 Claims, 15 Drawing Sheets

(56) References Cited

OTHER PUBLICATIONS

Search Report issued in GB Application No. 1517893.2, dated Aug. 23, 2016, 4 pages.
Broadwith, "Solving iron's solubility problem," Chemistry World, Dec. 2014, http://www.rsc.org/chemistryworld/2014/12/solving-iron-solubility-problem-profile-mrc, 4 pages.

(a)

(b)

(c)

METHODS FOR PRODUCING CARBOXYLATE LIGAND MODIFIED FERRIC IRON HYDROXIDE COLLOIDS AND RELATED COMPOSITIONS AND USES

CROSS REFERENCE TO RELATED APPLICATIONS

This application is a continuation of U.S. application Ser. No. 15/765,367, filed Apr. 2, 2018, which is a national phase entry pursuant to 35 U.S.C. § 371 of International Application No. PCT/EP2016/074022, filed Oct. 7, 2016, which claims the benefit of priority of GB Application No. 1517893.2, filed Oct. 9, 2015, each of which is incorporated by reference herein in its entirety for any purpose.

FIELD OF THE INVENTION

The present invention relates to methods for producing carboxylate ligand modified ferric iron hydroxides, and in particular to methods for recovering carboxylate ligand modified ferric iron hydroxide colloids that employ non-aqueous solvents. The present invention further relates to iron supplements and compositions comprising carboxylate ligand modified ferric iron hydroxides and their use in a method of treating iron deficiency anaemia.

BACKGROUND OF THE INVENTION

Despite considerable global efforts with oral iron supplementation and fortification, iron deficiency remains the most common and widespread nutritional disorder in the world. A key reason for this failure is that, to address iron deficiency, oral iron supplementation needs to be well tolerated, cheap, safe and effective. However, currently available preparations fail in at least one of these criteria. Simple ferrous iron [Fe(II)] salts are most commonly used as these are inexpensive and the iron is well absorbed. However, these are poorly tolerated and indeed appear to enhance systemic infection rates, may induce undesirable changes to commensal bacteria of the colon and increase pro-inflammatory signalling of the gut epithelium. Some forms of ferric iron [Fe(III)] (e.g. ferric pyrophosphate) are considered safer and better tolerated in the gut lumen than Fe(II), but have the disadvantage that they are poorly absorbed.

As examples of prior art iron supplements, WO 2005/094203 (Navinta) and WO 2005/000210 (Chromaceutical) relate to processes for making sodium ferric gluconate complexes (Ferrlecit™) for use as an intravenously administered iron supplements. These high molecular weight iron saccharidic complexes are formed when the surface of freshly precipitated iron hydroxide particles are coated with gluconate molecules, and subsequently form agglomerated mixtures of secondary complexes. US 2005/0256328 (Justus & Hanseler) also describe similar ferric gluconate complexes for intravenous delivery. WO 2004/07444 and US 2008/0274210 (Globoasia LLC) describe phosphate binding materials based on stoichiometric ferric citrate coordination complexes.

WO 2008/096130 (Medical Research Council) describes ferric iron oxo-hydroxide colloids that are modified synthetically so that dietary carboxylic acid ligands are non-stoichiometrically incorporated into the iron oxo-hydroxide structure. These colloidal ligand modified iron oxo-hydroxides, in which the mineral phase is disrupted, mimic the ferritin core—a natural dietary source of iron—and thus are well absorbed in humans with few or no side effects, providing a safe and efficacious oral iron supplement. The ligand modified ferric oxo-hydroxides described in WO 2008/096130 include nanoparticles of iron hydroxide modified with adipate (A) and tartrate (T) carboxylate ligands in a 1:1:2 T:A:Fe molar ratio (Iron Hydroxide Adipate Tartrate or "IHAT", see http://www.rsc.org/chemistryworld/2014/12/solving-iron-solubility-problem-profile-mrc). These materials are shown to be alternative safe iron delivery agents and their absorption in humans correlated with serum iron increase ($P<0.0001$) and direct in vitro cellular uptake ($P=0.001$), but not with gastric solubility. IHAT also showed ~80% relative bioavailability to Fe(II) sulfate in humans and, in a rodent model, IHAT was equivalent to Fe(II) sulfate at repleting haemoglobin. Furthermore, IHAT did not accumulate in the intestinal mucosa and, unlike Fe(II) sulfate, promoted a beneficial microbiota. In cellular models, IHAT was 14-fold less toxic than Fe(II) sulfate/ascorbate, itself has minimal acute intestinal toxicity in cellular and murine models and shows efficacy at treating iron deficiency anaemia (Pereira et al., Nanoparticulate iron(III) oxo-hydroxide delivers safe iron that is well absorbed and utilised in humans, Nanomedicine, 10(8): 1877-1886, 2014). Other papers describing IHAT and its uses for treating iron deficiency include Aslam, et al., Ferroportin mediates the intestinal absorption of iron from a nanoparticulate ferritin core mimetic in mice (FASEB J. 28(8):3671-8, 2014) and Powell et al., A nano-disperse ferritin-core mimetic that efficiently corrects anaemia without luminal iron redox activity (Nanomedicine. 10(7):1529-38, 2014).

IHAT materials are produced in WO 2008/096130 by co-precipitating ferric iron ions and the organic acids by raising the pH of an aqueous solution of the components from a pH at which they are soluble to a higher pH at which polymeric ligand modified ferric oxo-hydroxide forms. The precipitate is then dried, either by oven drying at 45° C. for 4-14 days or freeze-drying at −20° C. and 0.4 mbar for a longer period, thereby producing ligand modified ferric oxo-hydroxide suitable for formulation as an iron supplement. However, the success of IHAT as a widely used supplement means that there is a need in the art to improve the methods used for the production of these materials, such that the materials are produced cheaply at scale.

SUMMARY OF THE INVENTION

Broadly, the present invention relates to improvements to methods for producing carboxylate ligand modified ferric iron hydroxides, and in a particular to methods for recovering and purifying carboxylate ligand modified ferric iron hydroxide colloids. Generally, the carboxylate ligands comprise one or more dicarboxylate ligands, such as tartrate, adipate and/or succinate.

Despite promising in vivo bioavailability and tolerability evidence, the lack of scalable and cheap manufacturing processes is an obstacle to widespread use of carboxylate ligand modified ferric iron oxo-hydroxide colloids. Centrifugation or filtration could be used for recovery, but due to the colloids' small size (Dv0.9 (i.e. 90%)<10 nm), ultracentrifugation or ultrafiltration would have to be employed, which have the disadvantage of being uneconomical at manufacturing scales. Therefore, the dry powders produced so far have been recovered by first synthesising a dispersion of small colloids and then evaporating the water. However, this strategy requires a lengthy drying step (typically requiring about a week at 45° C.), with the result that it is energy intensive and promotes unwanted particle agglomeration, that is part of the material may not re-disperse once back in water, reducing intestinal bioavailability. In addition, the prior art process leads to the recovery of soluble reaction products (e.g. NaCl) and unbound carboxylate ligands with the iron colloids, and consequently the iron content in the powder (% w/w) is reduced as it is diluted by all the unused reactant materials. On the one hand, such low iron content is disadvantageous in oral iron supplementation since large pill masses need to be administered, which may impact negatively on patient compliance. On the other hand, it might be expected that the unused reactant materials contribute to the iron colloid particles remaining disperse and thus facilitating the iron availability and absorption. The ideal situation would be to meet both of these conflicting goals by removing unused reactant materials and retaining the particles of carboxylate ligand modified ferric iron hydroxides in a form in which they are bioavailable.

Surprisingly, we have found that ethanolic recovery of carboxylate ligand modified ferric iron hydroxide colloid overcomes all of these problems and provides a rapid, cheap process to produce a dry powder from the synthesised iron material suitable for formulation. This dry material retains its colloidal properties and is sufficiently concentrated to be capable of being given as a single capsule, tablet or powder for therapeutic supplementation, while removing unused reactant materials. The experiments described below also show that the materials recovered by using water miscible non-aqueous solvents such as ethanol had appropriate dissolution rates, and in some cases dissolved more rapidly that the corresponding oven-dried materials. Other water miscible non-aqueous solvents were found to be capable of providing similar results, in particular non-aqueous solvents such as methanol and acetone. The present inventors found that these methods produce carboxylate ligand modified ferric iron oxo-hydroxides materials having smaller primary particle sizes as compared to the prior art methods which are therefore more easily dissolved under lysosomal conditions within intestinal cells, and hence which have improved bioavailability via oral delivery. It should be noted that these properties differ from the iron supplements for intravenous delivery, such as those disclosed in WO 2005/094203, WO 2005/000210 and US 2005/0256328, as the intravenous materials need to be sufficiently stable not to dissolve rapidly in circulation as this would cause the significant patient toxicity.

Additionally, as the methods lead to a reduction in the carboxylate content of the materials, the effect of this is to increase the overall iron content present in the materials on a percentage weight for weight basis. Finally, despite the reduction in the carboxylate content, the methods help to produce materials in which aggregation and/or agglomeration of a fraction of the dried material is reduced.

Accordingly, in a first aspect, the present invention provides a method of producing a carboxylate ligand modified ferric iron hydroxide formulation, the method comprising
mixing a colloidal suspension of the carboxylate ligand modified ferric iron hydroxide in a water miscible non-aqueous solvent to cause the carboxylate ligand modified ferric iron hydroxide to agglomerate;
recovering the agglomerated carboxylate ligand modified ferric iron hydroxide; and
drying the carboxylate ligand modified ferric iron hydroxide to produce the carboxylate ligand modified ferric iron hydroxide formulation, wherein the carboxylate ligand comprises one or more dicarboxylate ligands.
Preferably, the water miscible non-aqueous solvent is selected from ethanol, methanol and/or acetone.

The method may optionally comprise the further step of carboxylate ligand modified ferric iron hydroxide formulation in a tablet or a capsule for oral delivery.

In a further aspect, the present invention provides an iron supplement tablet, capsule or powder comprising a carboxylate ligand modified ferric iron hydroxide composition as obtainable by the method described herein.

In a further aspect, the present invention provides a carboxylate ligand modified ferric iron hydroxide material having a three dimensional polymeric structure in which the carboxylate ligands are non-stoichiometrically substituted for the oxo or hydroxy groups of the ferric iron hydroxide so that some of the ligand integrates into the solid phase by formal metal-ligand bonding, wherein the three dimensional polymeric structure of the carboxylate ligand modified ferric iron hydroxide is such that the substitution of the oxo or hydroxy groups by the carboxylate ligands is substantially random, and/or wherein on dispersion in water the material produces a microparticulate ferric iron fraction comprising less than 3.0% of the total ferric iron present in the material.

In a further aspect, the present invention provides an iron supplement tablet, capsule or powder comprising a carboxylate ligand modified ferric iron hydroxide composition or a carboxylate ligand modified ferric iron hydroxide material of the present invention for use in a method of treating iron deficiency anaemia, iron deficiency and anaemia of chronic disease. These materials and compositions are preferably formulated for oral delivery.

Embodiments of the present invention will now be described by way of example and not limitation with reference to the accompanying figures. However various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

DETAILED DESCRIPTION

Figure 1:
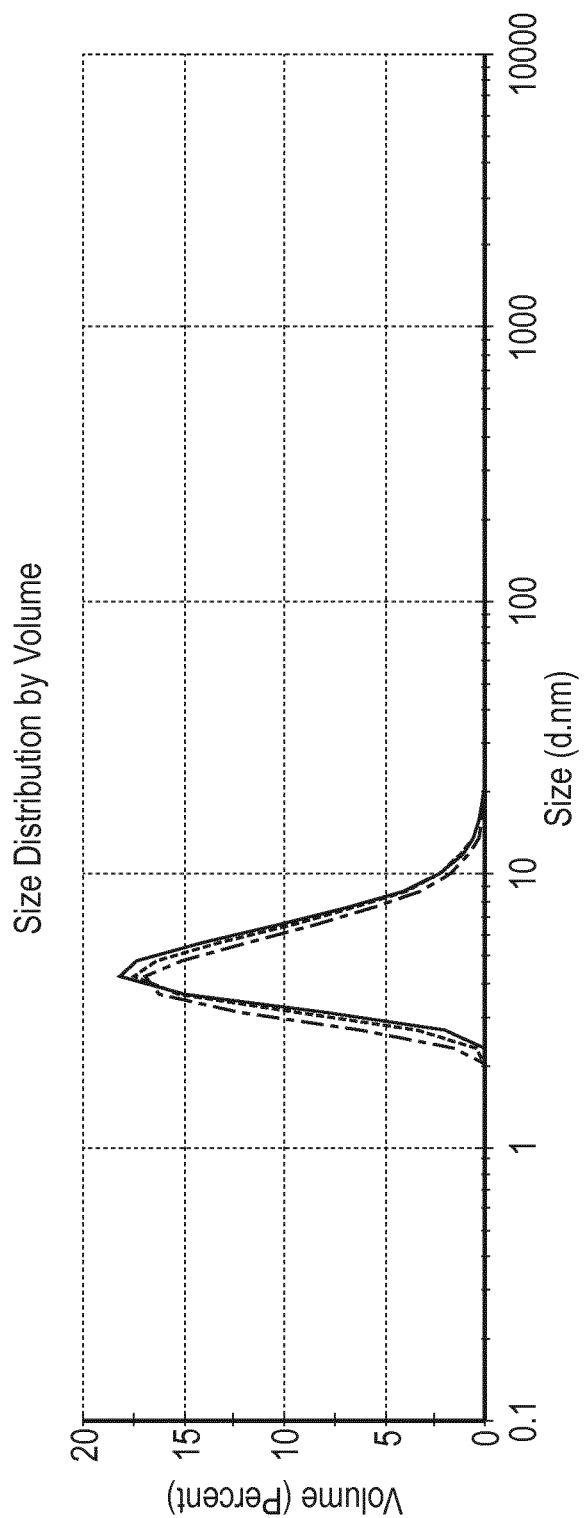
FIG. 1. Size distribution of an IHAT suspension (produced as per Example 1).

Production of Carboxylate Ligand Modified Ferric Iron Hydroxides

The carboxylate ligand modified ferric iron hydroxides may be produced under specific conditions by dissolving a suitable ferric iron [Fe(III)] salt and then inducing the formation of polymeric iron hydroxides in which a proportion of the carboxylate ligands become integrated into the solid phase through formal metal-iron (M-L) bonding, i.e. not all of the ligand (L) is simply trapped or adsorbed in the bulk material. The bonding of the metal ion in the materials can be determined using physical analytical techniques such as X-ray diffraction (XRD), which demonstrates disruption of mineral phase, i.e. with peak shifts and band broadening due increased amorphousness resulting from ligand incorporation in the primary particle.

In the carboxylate ligand modified iron hydroxides disclosed herein, the presence of formal metal ion-ligand bonding is one feature that distinguishes the materials from other products such as "iron polymaltose" (Maltofer) in which particulate crystalline iron hydroxide is surrounded by a sugar shell formed from maltose and thus is simply a mixture of iron oxo-hydroxide and sugar at the nano-level (Heinrich (1975); Geisser and Müller (1987); Nielsen et al (1994; U.S. Pat. No. 3,076,798); US2006/0205691).

In addition, the carboxylate ligand modified ferric iron hydroxides of the present invention are solid phase metal poly oxo-hydroxides modified by non-stoichiometric ligand incorporation. This distinguishes them from the numerous metal-ligand classical coordination complexes that are well reported in the art (WO 03/092674, WO 06/037449) which are stoichiometric. Although generally soluble, such complexes can be precipitated from solution at the point of supersaturation, for example ferric trimaltol, Harvey et al. (1998), WO 03/097627; ferric citrate, WO 04/074444, US 2008/0274210 and ferric tartrate, Bobtelsky and Jordan (1947) and, on occasions, may even involve stoichiometric binding of hydroxyl groups (for example, ferric hydroxide saccharide, U.S. Pat. No. 3,821,192).

Without modification, the primary particles of the carboxylate ligand modified ferric iron hydroxides used herein have ferric iron oxide cores and ferric hydroxide surfaces and within different disciplines may be referred to as metal oxides or metal hydroxides. The use of the term 'oxohydroxy' or 'oxo-hydroxide' may be used interchangeably and is intended to recognise these facts without any reference to proportions of oxo or hydroxy groups. As described herein, the carboxylate ligand modified ferric iron hydroxides of the present invention are altered at the level of the primary particle of the metal hydroxide with at least some of the ligand being introduced into the structure of the primary particle, i.e. leading to doping or contamination of the primary particle by the ligand. This may be contrasted with the formation of nano-mixtures of metal oxo-hydroxides and an organic molecule, such as iron saccharidic complexes, in which the structure of the core is not so altered.

The primary particles of the carboxylate ligand modified ferric iron hydroxides materials described herein are generally produced by precipitation. The use of the term "precipitation" often refers to the formation of aggregates or agglomerates of materials that do separate from solution by sedimentation or centrifugation. Here, the term "precipitation" is intended to describe the formation of all solid phase material, including agglomerates or other solid phase materials that remain as non-soluble moieties in suspension, whether or not they be particulate, colloidal or sub-colloidal and/or nanoparticulates or yet smaller clusters.

In the present invention, reference may be made to the carboxylate ligand modified ferric iron hydroxides having three dimensional polymeric structures that generally form above the critical precipitation pH. As used herein, this should not be taken as indicating that the structures of the materials are polymeric in the strict sense of having a regular repeating monomer unit because, as has been stated, ligand incorporation is, except by co-incidence, non-stoichiometric. Without wishing to be bound by any particular theory, the inventors believe that the carboxylate ligand species is introduced into the solid phase structure by substituting for oxo or hydroxy groups of the forming two dimensional iron oxo-hydroxide chains which then cross-link to form three dimensional structures and so the ligand leads to a change in solid phase order. In some cases, for example the production of the ferric iron materials exemplified herein, the ligand species may be introduced into the solid phase structure by the substitution of oxo or hydroxy groups by ligand molecules in a manner that decreases overall order in the solid phase material. While this still produces solid carboxylate ligand modified ferric iron hydroxides that in the gross form have one or more reproducible physicochemical properties, the materials have a more amorphous nature compared, for example, to the structure of the corresponding unmodified metal oxo-hydroxide. The presence of a more disordered or amorphous structure can readily be determined by the skilled person using techniques well known in the art. One exemplary technique is transmission electron microscopy (TEM). High resolution transmission electron microscopy allows the crystalline pattern of the material to be visually assessed. It can indicate the primary particle size and structure (such as d-spacing), give some information on the distribution between amorphous and crystalline material, and show that the material possesses a structure consistent with a 2-line ferrihydrite-like structure even when modified. Using this technique, it is apparent that the chemistry described above increases the amorphous phase of materials described herein compared to corresponding materials without the incorporated ligand. This may be especially apparent using high angle annular dark field aberration-corrected scanning transmission electron microscopy due to the high contrast achieved while maintaining the resolution, thus allowing the surface as well as the bulk of the primary particles of the material to be visualised.

Additionally or alternatively, upon ligand modification, the kinetics of dissolution of the carboxylate ligand modified ferric iron hydroxides are accelerated, for example as illustrated in the lysosomal assay, compared to the corresponding materials without the incorporated ligand. Examples of the properties that can be usefully modulated for materials used for iron supplementation or fortification include: dissolution (rate and pH dependence), adsorption and absorption characteristics, reactivity-inertness, melting point, temperature resistance, particle size, surface charge, density, light absorbing/reflecting properties, compressibility, colour and encapsulation properties. Examples of properties that are particularly relevant to the field of supplements or fortificants are physicochemical properties selected from one or more of a dissolution profile, an adsorption profile or a reproducible elemental ratio. In this context, a property or characteristic may be reproducible if replicate experiments for ethanolic recovery are reproducible within a standard deviation of preferably ±20%, and more preferably ±10%, and even more preferably within a limit of ±5%.

The dissolution profile of the solid ligand-modified poly oxo-hydroxy metal ion materials can be represented by different stages of the process, namely dispersion or re-suspension. The term dissolution is used to describe the passage of a substance from solid to soluble phase.

In the present invention, the carboxylate ligand modified ferric iron hydroxide materials described herein differ from prior art materials, for example IHAT produced by oven-drying or ultrafiltration, in having improved dispersion properties when the materials are resuspended in water. This can be assessed using the protocol described in the examples below in which a homogeneous aliquot of a suspension of the materials is taken and then the soluble, nanoparticulate and microparticulate ferric iron fractions separated by centrifugation (microparticulate fraction sediments) and ultrafiltration (soluble phase passes the filter). Any centrifugable phase formed may be separated from the solution by centrifugation (e.g. for 10 minutes at 13000 rpm; benchtop centrifuge). The iron concentration in the supernatant fraction may be determined by inductively coupled plasma optical emission spectrometry (ICP-OES). To differentiate between soluble iron and colloidal iron (non-centrifugable particles) in the supernatant, ultrafiltration may be used for example using a Vivaspin 3,000 Da molecular weight cut-off polyethersulfone membrane and the fraction again analysed by ICP-OES.

After they have been dried, when the carboxylate ligand modified ferric iron hydroxides materials of the present invention are dispersed in water at 40 mM Fe they produce small amounts or substantially no microparticulate fraction, with the ferric iron phase distribution being between soluble material and a nanoparticulate fraction, for example they will contain a microparticulate ferric iron fraction that has less than 5.0%, 4.0% 3.0%, 2.0%, 1.5%, 1.0%, 0.5% or 0.25% of the total iron present in the materials, and preferably substantially no microparticulate iron. This may be contrasted with the corresponding oven dried materials which disperse to produce a microparticulate ferric iron fraction containing about 5 to 10% of the total iron content.

Accordingly, the present invention provides a carboxylate ligand modified ferric iron hydroxide material having a three dimensional polymeric structure in which the carboxylate ligands are non-stoichiometrically substituted for the oxo or hydroxy groups of the ferric iron hydroxide so that some of the ligand integrates into the solid phase by formal metal-ligand bonding, wherein the three dimensional polymeric structure of the carboxylate ligand modified ferric iron hydroxide is such that the substitution of the oxo or hydroxy groups by the carboxylate ligands is substantially random, and wherein on dispersion in water the material produces a microparticulate ferric iron fraction comprising less than 3% of the total ferric iron present in the material.

In the carboxylate ligand modified iron hydroxides produced by the methods disclosed herein, the carboxylate ligands may be one, two, three or four or more carboxylate ligands in the form of the carboxylate ion or the corresponding carboxylic acid. Generally, the ligand is a dicarboxylic acid ligand, and may be represented by the formula HOOC—$R_1$—COOH (or an ionised form thereof), where $R_1$ is an optionally substituted $C_{1-10}$ alkyl, $C_{1-10}$ alkenyl or $C_{1-10}$ alkynyl group. The use of ligands in which $R_1$ is a $C_{1-10}$ alkyl group, and more preferably is a $C_{2-6}$ alkyl group, is preferred. Preferred optional substituents of the $R_1$ group include one or more hydroxyl groups, for example as present in malic acid. These ligands include carboxylic acids such as adipate/adipic acid, tartrate/tartaric acid, glutarate/glutaric acid, malate/malic acid, succinate/succinic acid, aspartate/aspartic acid, pimelate/pimelic acid, citrate/citric acid, lactate/lactic acid or benzoate/benzoic acid. In the production of some preferred materials, such as IHAT, two different ligands are used, such as adipate/adipic acid and tartrate/tartaric acid. Other examples of preferred combinations of ligands include tartrate/tartaric acid and succinate/succinic acid. Particularly preferred materials are formed using the following molar ratios of ligands and Fe(III):

| Material | Ligands | Molar Ratio ligand:Fe |
|---|---|---|
| Nano Fe (III) (a) "IHAT" | Tartaric acid (T) Adipic acid (A) | 1:1:2 (T:A:Fe) |
| Nano Fe (III) (b) | Tartaric acid (T) Succinic acid (S) | 1:1:2 (T:S:Fe) |
| Nano Fe (III) (c) | Tartaric acid (T) Succinic acid (S) | 1:6:2 (T:S:Fe) |

Without wishing to be bound by any particular theory, the present inventors believe that in IHAT it is the tartrate/tartaric acid ligands that are mostly responsible for the disruption of the iron hydroxide structure of the primary particles (Nanomedicine, 10(8): 1877-1886, 2014). In view of this observation, in a further embodiment, the carboxylate ligand modified iron hydroxides may be modified by tartrate/tartaric acid as the sole carboxylate ligand.

The ratio of the ferric iron ion(s) to the carboxylate ligands can be varied according to the methods disclosed herein and may vary one or more properties of the materials. Generally, the useful ratios of M:L will be between 10:1, 5:1, 4:1, 3:1, 2:1 and 1:1 and 1:2, 1:3, 1:4, 1:5 or 1:10, and preferably between 4:1 and 1:1. By way of example, in the preferred IHAT materials, the concentration of ferric iron ions may be between 20 mM and 80 mM, the concentration of adipate is between 10 mM and 40 mM and the concentration of tartrate is between 10 mM and 40 mM. In the synthesis of IHAT, a concentration of ferric iron of about 40 mM was used with 20 mM adipic acid and 20 mM tartaric acid. Alternatively, and in particular where different ratios of the components are used, the concentration of ferric iron may be between 20 mM and 500 or 1000 mM, the concentration of adipate may be between 10 mM and 150 mM and the concentration of tartrate may be between 10 mM and 250 mM.

In the case of materials using tartrate/tartaric acid as the sole carboxylate ligand, or where adipate is capped at its maximum aqueous concentration (e.g. 150 mM at room temperature), a higher concentration of ferric iron ions may be used between a lower limit 80 mM, 100 mM and 120 mM and an upper limit of 250 mM, 350 mM, 500 mM and 1000 mM, optionally in combination with a concentration of tartrate/tartaric acid between 20 mM and 250 mM or 500 mM.

The present invention may employ any way of forming hydroxide ions at concentrations that can provide for hydroxy surface groups and oxo bridging in the formation of the carboxylate ligand modified ferric iron hydroxide materials. Examples include but are not limited to, alkali solutions such as sodium hydroxide, potassium hydroxide and sodium bicarbonate.

The methods of the present invention produce a suspension of particles having a size distribution (as a percentage of particle volume) between about 1 nm and 20 nm in diameter, with the majority of the particles (in a volume-based distribution) having a size distribution between about 2 nm and 10 nm in diameter. Within a given size range, it is preferred that at least 75% of the nanoparticles of carboxylate ligand modified ferric iron hydroxide have an average diameter in the range, and more preferably that at least 90% of the nanoparticles of carboxylate ligand modified ferric iron hydroxide have an average diameter in the range. The hydrodynamic particle size of colloidal suspensions may be determined by dynamic light scattering (DLS), for example using a Zetasizer Nano-ZS (Malvern Instruments, UK). The reduction in crystallite size in non-aqueous solvent recovered materials is too subtle to be determined by dynamic light scattering since this technique also captures size of the surrounding water shell in the redispersed particles. Instead, TEM or XRD (attenuation and/or shift of the ferrihydrite band) should be employed.

The exact conditions of mixing and precipitation of the carboxylate ligand modified ferric iron hydroxides will vary depending upon the desirable characteristics of the solid material. Typical variables are:

(1) Starting pH (i.e. the pH at which metal ion and ligand species are mixed). This will generally be a different pH to that at which hydroxy polymerisation commences. Preferably, it is a more acidic pH, more preferably below a pH of 2.

(2) The pH at which polymerisation of the carboxylate ligand modified ferric iron hydroxide commences. This is always a different pH to that of the starting pH. Preferably, it is a less acidic pH and most preferably above a pH of 1.5 or 2.

(3) Final pH. This will always promote precipitation and may promote agglomeration of the carboxylate ligand modified ferric iron hydroxides and preferably will be a higher pH than the pH at which hydroxy polymerisation commences. In this case, a final pH between pH 7.0 and 9.0, and more specifically between pH 7.4 and 8.5 is preferred.

(4) Rate of pH change from commencement of polymerisation of the carboxylate ligand modified ferric iron hydroxide to completion of reaction. This will occur within a 24 hour period, preferably within an hour period and most preferably within 20 minutes.

(5) Concentrations of metal ions and ligand species. While the concentration of OH is established by the pH during hydroxy polymerisation, the concentrations of total metal ion and total ligand species in the system will be fixed by the starting amounts in the mixture and the final solution volume. Typically, this will exceed $10^{-6}$ molar for both metal ion and ligand species and more preferably it will exceed $10^{-3}$ molar. Concentrations of metal ion and ligand species are independent and chosen for one or more desired characteristics of the final material.

(6) Solution phase. The preferred solution for this work is aqueous and most preferably is water.

(7) Temperature. The preferred temperature is above 0 and below 100° C., typically between room temperature (20-30° C.) and 50° C. or 100° C., most typically at room temperature.

(8) Ionic strength. Electrolyte such as, but not limited to, potassium chloride and sodium chloride, may be used in the procedure. The ionic strength of the solution may thus range from that solely derived from the components and conditions outlined in (1)-(8) above or from the further addition of electrolyte which may be up to 10% (w/v), preferably up to 2%, and most preferably <1%.

After separation of the precipitated material, it may optionally be dried before use of further formulation. The dried product may, however, retain some water and be in the form of a hydrated carboxylate ligand modified ferric iron hydroxide. It will be apparent to those skilled in the art that at any of the stages described herein for recovery of the solid phase, excipients may be added that mix with the carboxylate ligand modified ferric iron hydroxides but do not modify the primary particle and are used with a view to optimising formulation for the intended function of the material.

Purification and Recovery of the Carboxylate Ligand Modified Ferric Iron Hydroxides The methods of the present invention enable the large scale production of carboxylate ligand modified ferric iron hydroxide formulation, and especially one in which the iron content is greater than that produced when oven drying is used. The methods also enable the carboxylate ligand modified ferric iron hydroxide to be separated from unreacted starting materials, such as free unreacted ligand, unreacted ferric iron ions, sodium ions, potassium ions and/or chloride ions, and by-products such as salts, which is not possible in the prior art oven drying methods.

The carboxylate ligand modified ferric iron hydroxide of the present invention generally have an iron content of at least 10% Fe (w/w), and may have an iron content of at least 15% Fe (w/w), or an iron content of at least 20% Fe (w/w), or an iron content of at least 25% Fe (w/w), or an iron content of at least 30% Fe (w/w). Lower levels of iron content are generally due to the presence of excess unreacted ligand or salt resulting from the synthesis of the materials. The choice of the iron content of the final formulation that includes the carboxylate ligand modified ferric iron hydroxide will be dependent on a range of factors, and a higher iron content as compared to oven dried materials may be advantageous in helping to reduce the size of tablets or capsules containing the carboxylate ligand modified ferric iron hydroxide, e.g. for improving ease of administration or helping with patient compliance. It will be obvious to those in the art that excipients including the same or different ligand(s) as in the synthesis could be mixed with the final product to provide advantageous formulation properties such as, but not restricted to, the prevention of aggregation or agglomeration or to alter powders flow properties in manufacturing or to aid tableting in manufacture.

As stated above, the methods of the present invention involve mixing a colloidal suspension of the carboxylate ligand modified ferric iron hydroxide with a water miscible non-aqueous solvent, generally ethanol, methanol or acetone, or mixtures thereof. In a preferred embodiment, the water miscible non-aqueous solvent is ethanol. Conveniently, the ratio of the volume of the water miscible non-aqueous solvent to the colloidal suspension of the carboxylate ligand modified ferric iron hydroxide is between 1:1 and 5:1. The present inventors found that the addition of water miscible non-aqueous solvents causes the carboxylate ligand modified ferric iron hydroxide to agglomerate enabling it to be separated from excess reaction products such as non-incorporated ligand as described above and then recovered, for example by centrifugation or filtration. After the material has been recovered, it may be dried. In the drying step, the time and/or temperature used are generally shorter and lower than the prior art oven drying and preferably the drying step takes 24 hours or less at 45° C. Other examples of water miscible non-aqueous solvents are described at https://en.wikipedia.org/wiki/List of water-miscible solvents.

Accordingly, in some aspects, the present invention may use a water miscible non-aqueous solvent, or mixtures thereof, other than ethanol, methanol and/or acetone, and especially water miscible non-aqueous solvent that are non-toxic or Generally Regarded As Safe (G.R.A.S.). This means that the water miscible non-aqueous solvents include: acetone, acetonitrile, butanol, 1,2-butanediol, 1,3-butanediol, 1,4-butanediol, diethanolamine, diethylenetriamine, dimethyl sulfoxide, ethanol, ethylamine, ethylene glycol, glycerol, methanol, methyl diethanolamine, 1-propanol, 1,3-propanediol, 1,5-pentanediol, 2-propanol, propylene glycol and triethylene glycol, and mixtures thereof.

Figure 14:
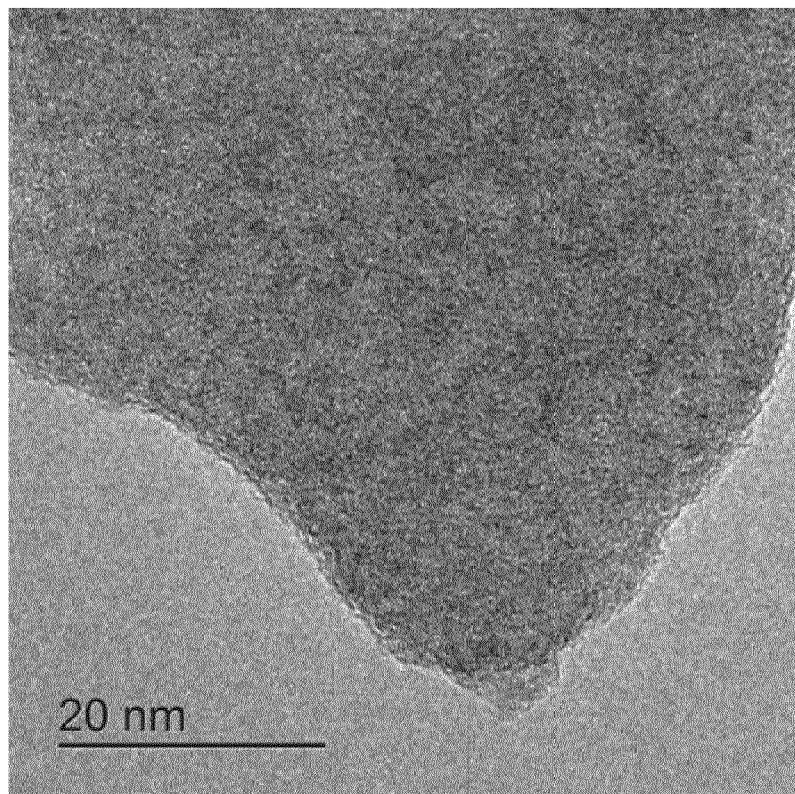
FIG. 14. TEM images of IHAT recovered using (a) ethanolic treatment, (b) oven drying and (c) ultrafiltration. The images show that the ethanolic recovered material was the finest grained and hence the most amorphous and with a smaller crystallite size. The materials recovered by oven drying and ultrafiltration were indistinguishable.
Figure 14:
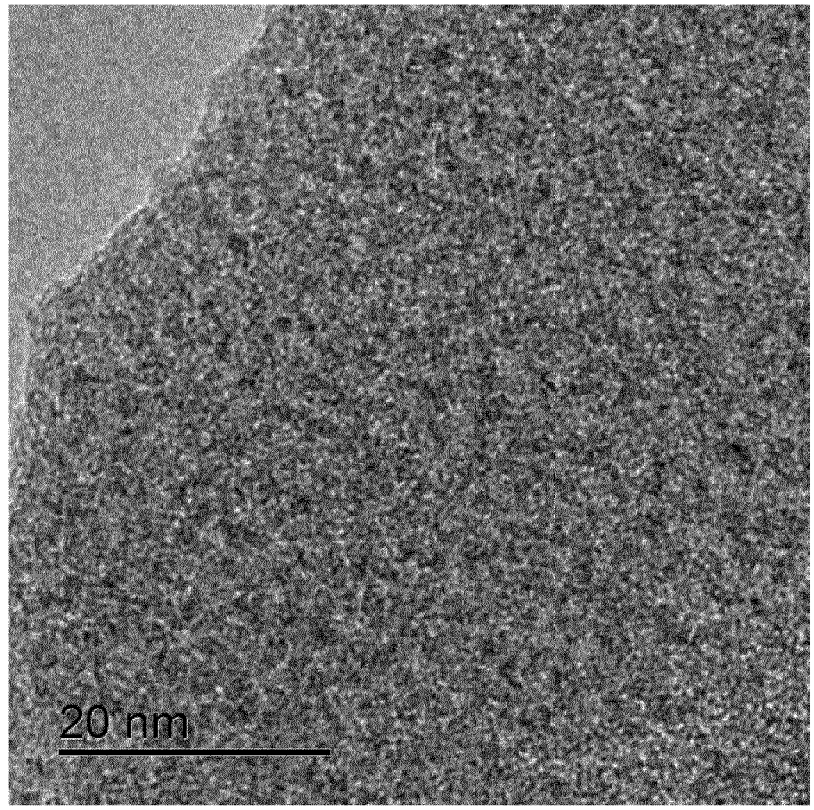
Figure 14:
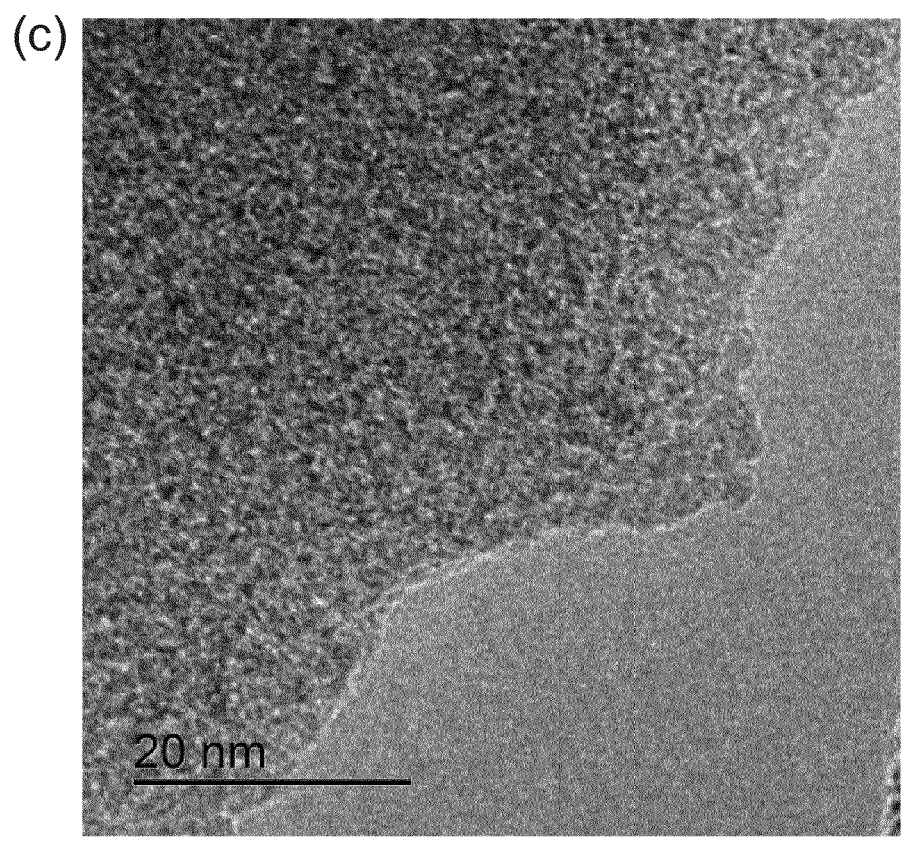

A further advantage of the present invention is that the carboxylate ligand modified ferric iron hydroxides are generally at least as amorphous and crystallite size at least as small as prior art materials because rapid drying of the water miscible non-aqueous solvent shortens the ageing process of a colloid that would otherwise occur if an aqueous suspension is dried using the slower approaches of the prior art. In general, these ageing processes increase the crystallinity or increase crystallite size or reduce the amorphousness of the materials. Without wishing to be bound by any particular theory, the present inventors believe that amorphous carboxylate ligand modified ferric iron hydroxides are required for good oral bioavailability. FIG. 14 shows that carboxylate ligand modified ferric iron hydroxides using water miscible non-aqueous solvent was more finely grained, and hence more amorphous, than the materials recovered using oven drying or ultrafiltration. The materials of the present invention are therefore likely to have improved in vivo bioavailability as compared to the prior art materials produced using oven drying or ultrafiltration.

After drying, the carboxylate ligand modified ferric iron hydroxide formulation will generally have a mean particle size between 1 and 20 nm, and more preferably between 1 and 10 nm.

Prior to formulating the carboxylate ligand modified ferric iron hydroxide, e.g. in a form for oral delivery, the method may comprise one or more additional processing steps. Examples of these include milling or micronizing the carboxylate ligand modified ferric iron hydroxide composition. The carboxylate ligand modified ferric iron hydroxide composition may then be mixed with one or more pharmaceutically acceptable excipients and then formed in a final form for oral delivery, for example by making tablets or capsules.

Formulations and Uses

The carboxylate ligand modified ferric iron hydroxides produced by the methods of the present invention may be formulated for use as supplements, and especially as therapeutic iron supplements. This means that the formulations may be mixed with one or more pharmaceutically acceptable excipients, carriers, buffers, stabilisers or other materials well known to those skilled in the art. Such materials should be non-toxic and should not interfere with the efficacy of the carboxylate ligand modified ferric iron hydroxides for iron supplementation.

The precise nature of the carrier or other component may be related to the manner or route of administration of the composition, in the present case generally via gastrointestinal delivery, in particular oral delivery. Pharmaceutical compositions for oral administration may be in tablet, capsule, powder, gel or liquid form. In some instances, the materials may be directly orally taken, while in other embodiments, they may be provided in a form suitable for mixing with food or drink and taken in this manner. The latter may be termed fortification but the terms supplement and supplementation are herein included to cover this as well as usual supplement practice.

Tablets are formed by compressing an active substance with components to enable the formation of the tablet and its dissolution after it has been taken by a subject. Accordingly, a tablet may include a solid carrier, such as gelatin or an adjuvant or carrier, a compressibility agent and/or a flowing agent. In the present invention, an iron supplement in the form of a tablet may comprise one or more of the carboxylate ligand modified ferric iron hydroxides (for example forming 5-60% (w/w) of the tablet) and one or more fillers, disintegrants, lubricants, glidants and binders (for example forming the remaining 40-95% (w/w) of the tablet). In addition, the tablet may optionally comprise one or more coatings, for example to modify dissolution of the tablet for either quick or sustained release, and/or one of more coatings to disguise the taste of the tablet or to make it easier for a subject to take orally.

Generally, capsules are formed by enveloping an active substance in a gelatinous envelope. As with tablets, capsules may be designed for quick or sustained release depending on the properties of the envelope or a coating provided on it. Release of the active substance may also be controlled by modifying the particle size(s) of the active substance contained with the envelope. Capsules are generally either hard shelled or soft shelled. Hard shelled capsules are typically made using gelatin to encapsulate the active substance and may be formed by processes such as extrusion or spheronisation. Hard shelled capsules may be formed by sealing together two half shells to form the final capsule. Soft shelled capsules are generally formed by suspending an active ingredient in oil or water and then forming the envelope around the drops of the liquid. Other components of capsules include gelling agents, plant polysaccharides, plasticizers, e.g. for modulating the hardness of the capsule, colouring agents, preservatives, disintegrants, lubricants and coatings.

The carboxylate ligand modified ferric iron hydroxides used in accordance with the present invention that are to be given to an individual are preferably administered in a "prophylactically effective amount" or a "therapeutically effective amount" (as the case may be, although prophylaxis may be considered therapy), this being sufficient to show benefit to the individual (e.g. bioavailability). The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

By way of example, iron supplements are generally administered at doses of between 100 mg Fe to 250 mg Fe per day, and often at doses between 50 mg Fe and 80 mg Fe (e.g. about 60 mg Fe) three times a day (t.d.s.). Single dosing may be possible using a sustained release formulation. Prophylactic supplementation may use lower doses, but it is desirable to have any dose containing as high a percentage of the active agent (iron) as possible as this will minimise the size of the dose (capsule, pill etc.). In this aspect, this invention minimises non-active ingredients, such as unreacted ligands, of the formulation and allows the active iron material to be well concentrated in the oral delivery dose.

The carboxylate ligand modified ferric iron hydroxides may be used as supplements for nutritional or medical benefit. In this area, there are three main examples:

(i) Therapeutic (prescription) supplements, which are generally administered orally for the treatment of indications including iron deficiency anaemia, iron deficiency and anaemia of chronic disease. The therapeutic administration of carboxylate ligand modified ferric iron hydroxides of the present invention may be in conjunction with other therapies, for example with the concomitant use of erythropoietin.

(ii) Nutritional supplements (self prescribed/purchased supplements) which are usually for oral delivery.

(iii) Fortificants. These may be traditional forms—in terms of being added to food prior to purchase—or more recent fortificant forms such as 'Sprinkles' which are added (like salt or pepper) to food at the time of ingestion.

In all formats, but most especially for fortificants, subsequent formulation, such as addition of a protective coating (e.g. lipid), may be necessary to make the material compatible with its intended usage. In addition, any of these supplemental forms can be co-formulated, either by incorporation within the material through use of co-formulated material(s) as ligand(s) or through trapping/encapsulation of said materials, or simply through co-delivery of said materials.

As described herein, one particular application of the carboxylate ligand modified ferric iron hydroxides of the present invention is for the treatment of mineral deficiencies, for example iron deficiency.

By way of example, the carboxylate ligand modified ferric iron hydroxides disclosed herein may be used to deliver iron to an individual for use in the prophylaxis or treatment of iron deficiency or iron deficiency anaemia which may be suspected, or diagnosed through standard haematological and clinical chemistry techniques. Iron deficiency and iron deficiency anaemia may occur in isolation, for example due to inadequate nutrition or due to excessive iron losses, or they may be associated with stresses such as pregnancy or lactation, or they may be associated with diseases such as inflammatory disorders, cancers and renal insufficiency. In addition, there is evidence that the reduced erythropoiesis associated with anaemia of chronic disease may be improved or corrected by the effective delivery of systemic iron and that co-delivery of iron with erythropoietin or its analogues may be especially effective in overcoming reduced erthropoietic activity. Thus, by way of further example, the ferric iron compositions disclosed herein may be used to deliver iron to an individual for use in the treatment of sub-optimal erythropoietic activity such as in anaemia of chronic disease. Anaemia of chronic disease may be associated with conditions such as renal insufficiency, cancer and inflammatory disorders. As noted above, iron deficiency may also commonly occur in these disorders so it follows that treatment through iron supplementation may address iron deficiency alone and/or anaemia of chronic disease.

EXAMPLES

Materials and Methods
Centrifugation

Recovery of agglomerates was carried out by centrifugation or ultrafiltration on a Mistral 6000 centrifuge at 4500 rpm. Phase speciation was carried out at 13000 rpm on a benchtop centrifuge.

Phase Speciation

A homogeneous aliquot (1 mL) of the suspension was collected and transferred to an Eppendorf tube. Any centrifugable phase formed was separated from the solution by centrifugation (10 minutes at 13000 rpm; benchtop centrifuge). The iron concentration in the supernatant fraction was then determined by inductively coupled plasma optical emission spectrometry (ICP-OES). To differentiate between soluble iron and colloidal iron (non-centrifugable particles) in the supernatant, a further 0.7 mL aliquot was ultrafiltered (Vivaspin 3,000 Da molecular weight cut-off polyethersulfone membrane) and again analysed by ICP-OES.

TEM

The sample was prepared for TEM by dispersing in methanol and drop-casting directly on holey carbon TEM support film (Cu-grid) and air-drying. Samples were analysed in the CM200 FEG-TEM.

XRD

Samples were crushed, and loaded in to standard plastic sample holders. The diffraction data were collected with a Bruker D8 Diffractometer using Cu Kα radiation, employing a Vantec detector. The scanning range was 5-75 degrees 2θ, with a step size of 0.15°; the total time for collection was 14 hours per sample.

Resuspension of Dried Powders

Powders produced as per examples above were resuspended in UHP water to the initial Fe concentration (ca. 40 mM) and particle size distribution (volume based) determined by dynamic light scattering.

Lysosomal Dissolution Assay

Dissolution rates under simulated lysosomal conditions were determined at pH 5.0±0.1 in a 10 mM citric acid, 0.15 M NaCl solution. The Fe material was added to the assay solution at an Fe concentration of ca. 1 mM and incubated for 360 min at room temperature. Phase speciation was carried out as per above.

Example 1: Synthesis of an Iron Hydroxide Adipate Tartrate (IHAT) Suspension 2.7 g KCl, 0.90 g tartaric acid and 0.88 g adipic acid were added to a beaker containing 240 mL ddH$_2$O. The mixture was stirred until all of the components dissolved. Then 100 mL of a ferric iron solution was added (200 mM FeCl$_3$·6H$_2$O, 0.5 mL conc. HCl in 60 mL ddH$_2$O). The final concentration of iron in the solution was 40 mM, KCl was 0.9% w/v and pH was below 2.0. NaOH was added drop-wise (from a 5M NaOH solution prepared in ddH2O) to this mixture, with constant stirring until 7.4<pH<8.5 was achieved. This resulted in a suspension that comprised small colloids (see FIG. 1) and was free of agglomerates. The process was carried out at room temperature (20-25° C.)

Example 2: Oven Drying of an IHAT Suspension (Comparative Example)

Suspensions produced as in Example 1 were air-dried in an oven at 45° C. Drying required typically about a week (4-14 days depending on the volume being dried). The dried material was milled by hand or micronized with a ball mill.

Example 3: Oven Drying of an Ultrafiltered IHAT Suspension

Reaction products, other than IHAT, and the unbound ligand fraction were removed from an IHAT suspension through ultrafiltration (20 mL capacity ultra-filters with a PES membrane; 3000 MWCO cut off). Ultrafiltration was carried out by transferring 20 mL of an IHAT suspension (produced as in Example 1) and spinning at 4500 RPM until less than 2 mL of colloidal concentrate was left. The ultrafiltrate (containing non-colloidal species) was then discarded, and the concentrate was diluted up to 20 mL with ddH$_2$O. This suspension was ultrafiltered again at 4500 rpm and the resulting ultrafiltrate was also discarded. Finally, the carboxylate-free colloidal concentrate was transferred to a petri dish and dried in an oven at 45° C. (3 days).

Example 4: Ethanolic Recovery

A suspension of IHAT produced as in Example 1 was diluted with ethanol at a proportion of 1:2 (15 mL IHAT+30 mL ethanol). Addition of ethanol resulted in immediate agglomeration of colloids and the resulting agglomerates centrifuged at 4600 rpm for 10 minutes. Next, the supernatant was discarded and the pellet—containing agglomerated IHAT—was dried for 24 hours in an oven at 45° C.

Example 5: Methanolic Recovery

The procedure was the same as in ethanolic recovery except methanol was used.

Example 6: Acetonic Recovery

The procedure was the same as in ethanolic recovery except acetone was used

Example 7: Synthesis of a Concentrated IHAT Suspension (200 mM Iron)

15.01 g tartaric acid and 14.61 g adipic acid were added to a beaker containing 800 mL ddH$_2$O. The mixture was stirred and moderately heated until all of the components dissolved. Once the carboxylate solution had returned to room temperature, 200 mL of a ferric iron solution (54.06 g FeCl$_3$.6H$_2$O in 200 mL ddH2O) was added to it. The final concentration of iron in the resulting solution was 200 mM and the pH was below 1.5. NaOH was then added drop-wise (from a 5M NaOH solution prepared in ddH$_2$O) to this mixture, with constant stirring until 7.8<pH<8.5 was achieved. This resulted in a dark suspension. The process was carried out at room temperature (20-25° C.)

Example 8: Ethanolic Recovery of Concentrated IHAT

The suspension of IHAT produced in Example 7 was diluted with 2 L ethanol. Addition of ethanol resulted in immediate agglomeration of colloids and the resulting agglomerates were centrifuged at 4600 rpm for 10 minutes. Next, the supernatant was discarded and the pellet—containing agglomerated IHAT—was dried for 24 hours in an oven at 45° C.

Figure 15:
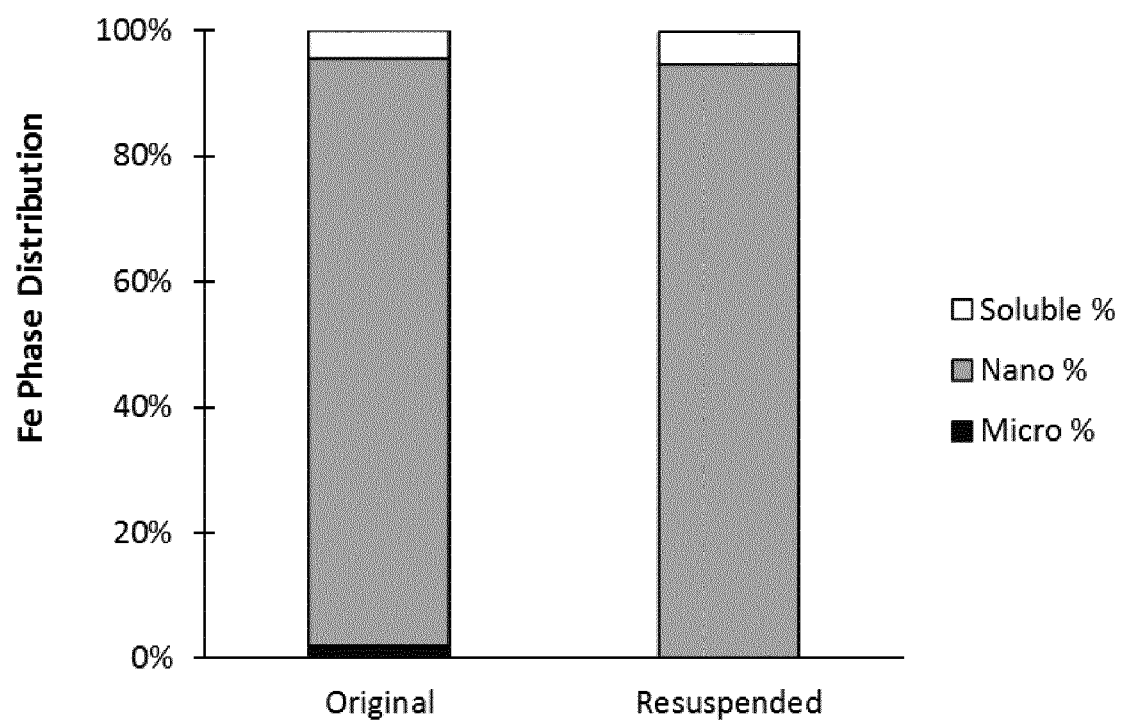
FIG. 15. Phase distribution of concentrated ethanolic IHAT before ("original"; as per Example 7) and after ethanolic recovery ("resuspended"; as per Example 8). Experimental details are provided in Example 9.
Figure 16:
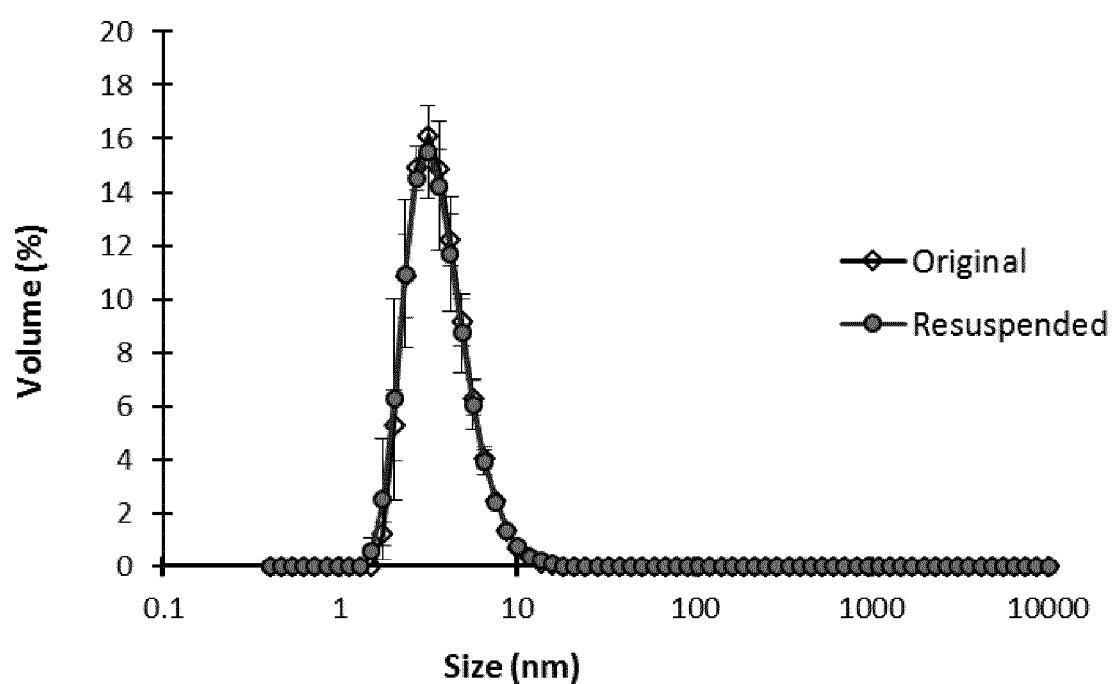
FIG. 16. Size distribution of concentrated ethanolic IHAT before ("original"; as per Example 7) and after ethanolic recovery ("resuspended"; as per Example 8). Experimental details are provided in Example 9. Each individual trace corresponds to the average of three analytical replicates (N=3; standard deviation bars shown).

Example 9: Characterisation of Concentrated IHAT Recovered by Ethanolic Precipitation An aliquot of the final suspension produced as in Example 7 was diluted 1:5 (ca 30 mM) and characterised for particle size and phase distribution prior to ethanolic precipitation (FIGS. 15 and 16; termed "original" in the figure legends). After ethanolically recovering and oven drying the suspension above (as per Example 8) a portion of the powder was resuspended to ca 30 mM (0.3682 g in 50 mL water). This suspension was then characterised for particle size and phase distribution (FIGS. 15 and 16; termed "resuspended" in the figure legends), showing that the material did resuspend to its original size and phase distribution. Iron content of the dry powder was determined to be 22.4±0.4% (w/w).

Results

Figure 2:
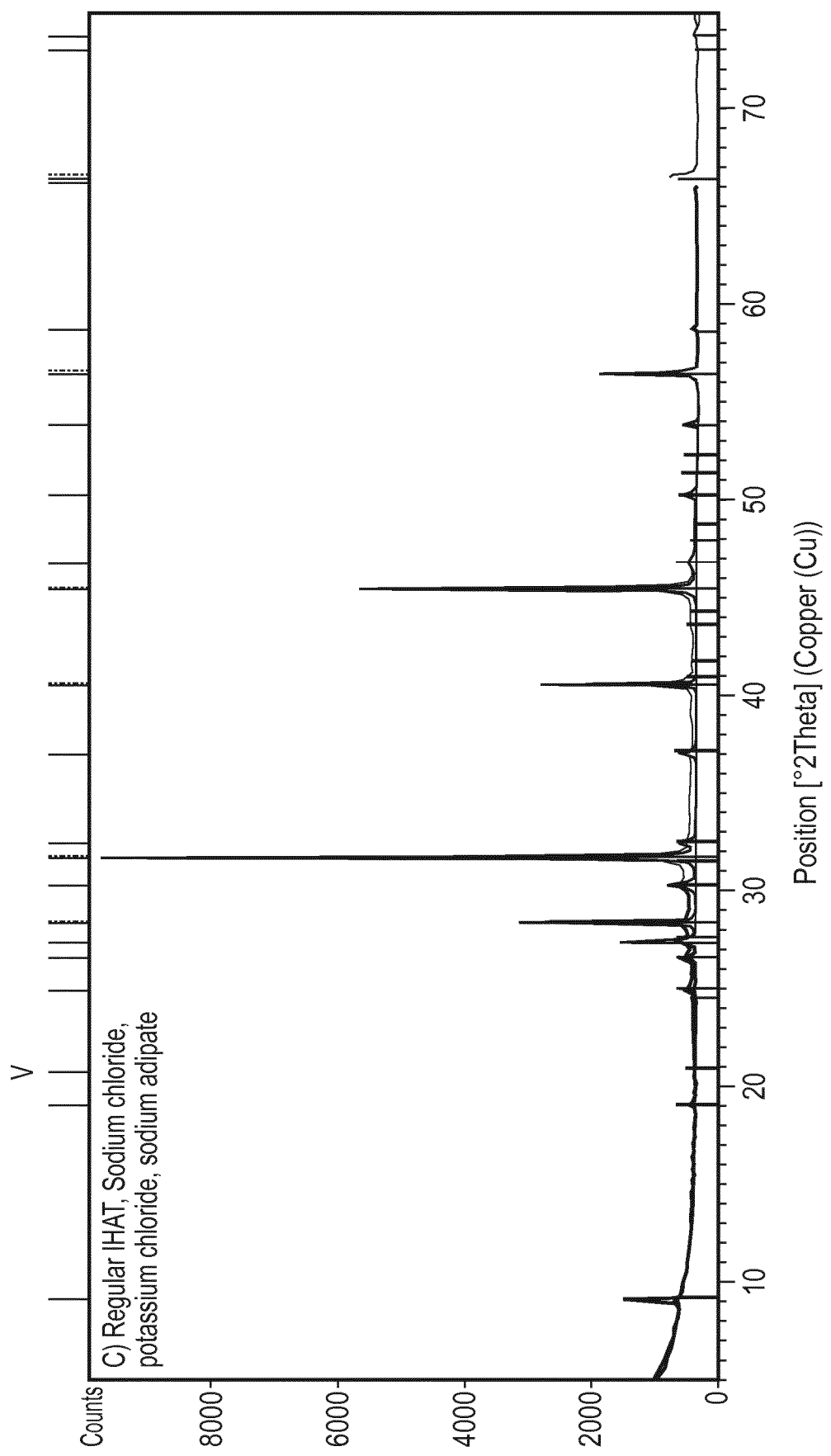
FIG. 2. X-ray diffractogram of an IHAT powder recovered by oven drying (as per Example 2). Top trace shows full scale with fitting of NaCl and KCl traces (key peaks indicated by vertical lines starting at the x axis). Bottom trace shows zoomed XRD pattern of disrupted ferrihydrite baseline, showing the presence of sharp diffraction peaks from potassium/sodium chloride and sodium adipate plus an underlying, broad, diffuse peak at ca. 33° 2-theta that is consistent with a modified ferrihydrite.
Figure 2:
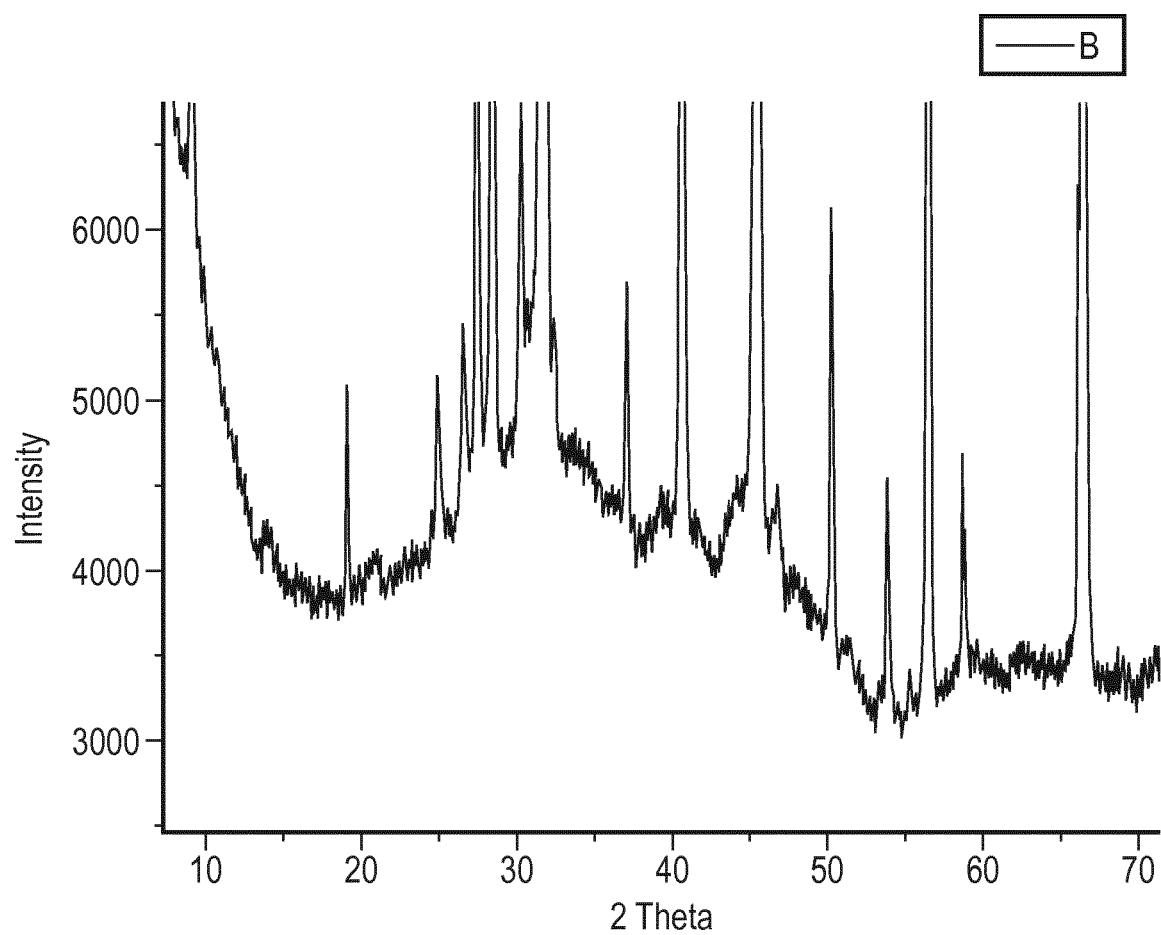
Figure 3:
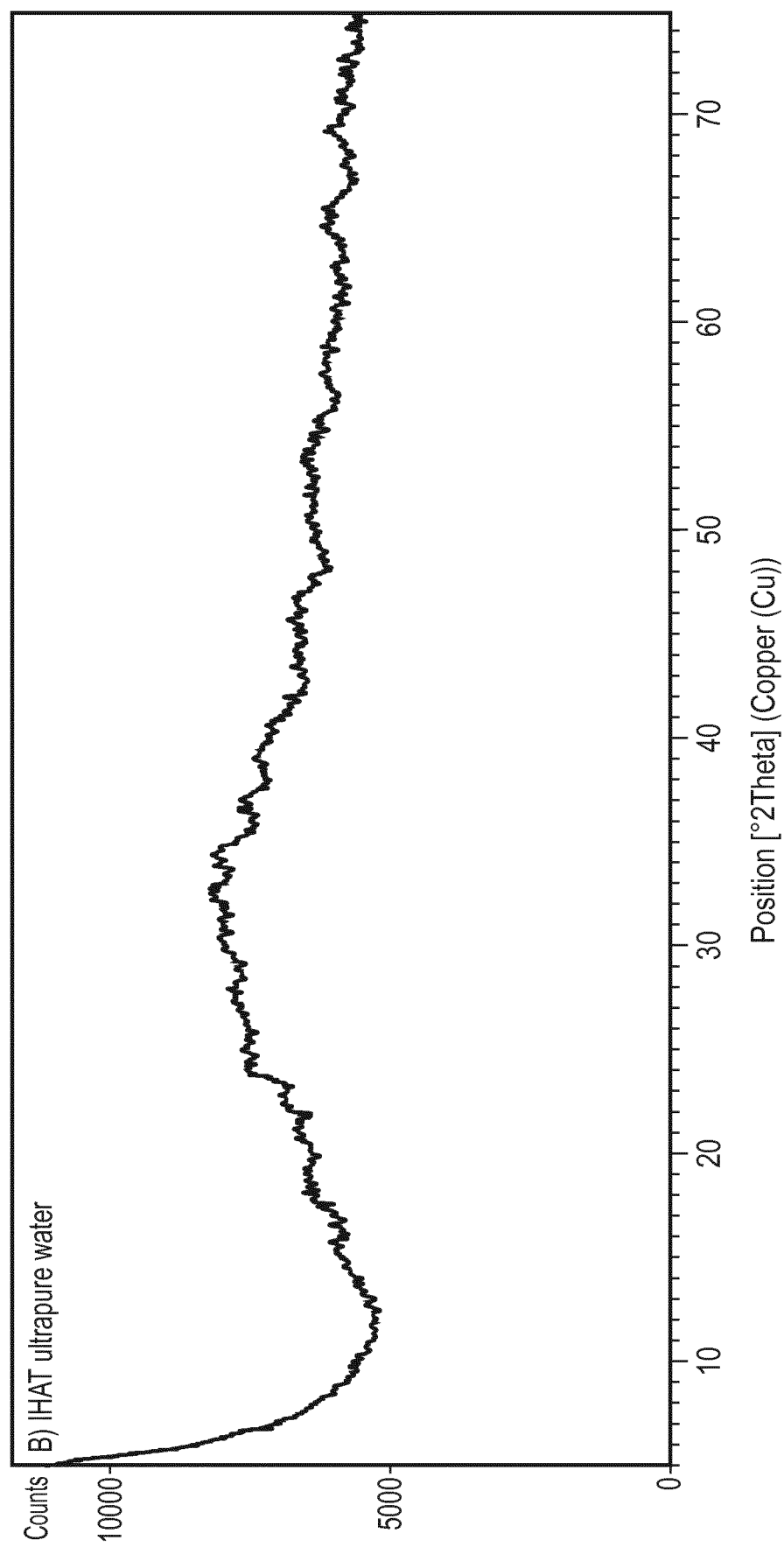
FIG. 3. X-ray diffractogram of an IHAT powder in which unbound ligands and reaction products (e.g. NaCl) were removed by ultrafiltration (as per Example 3). Trace shows the presence of one very broad and diffuse diffraction 'peak' centred around 32 to 33° 2-theta) that is consistent with a modified ferrihydrite.

Iron Hydroxide Adipate Tartrate (IHAT) as per previous disclosures is produced as a suspension of small iron oxo-hydroxide colloids (FIG. 1; Example 1). These materials are ferrihydrite-based particles where the mineral phase of the iron hydroxide has been disrupted by tartrate ligands mostly (FIG. 2). Thus far, dry IHAT materials have been produced by simply evaporating water from the suspension (as per Example 2). However, this is a lengthy and energetically costly process. Also, as stated above, the 'trapping' of unbound carboxylate ligands in the final powder produces formulations with low iron content (i.e. large pills are required). Alternatively, ultrafiltration can be used to remove unbound soluble species prior to drying (FIG. 2) and consequently increase iron content (Table 1) but this is also a costly strategy that cannot be easily scaled up.

Figure 4:
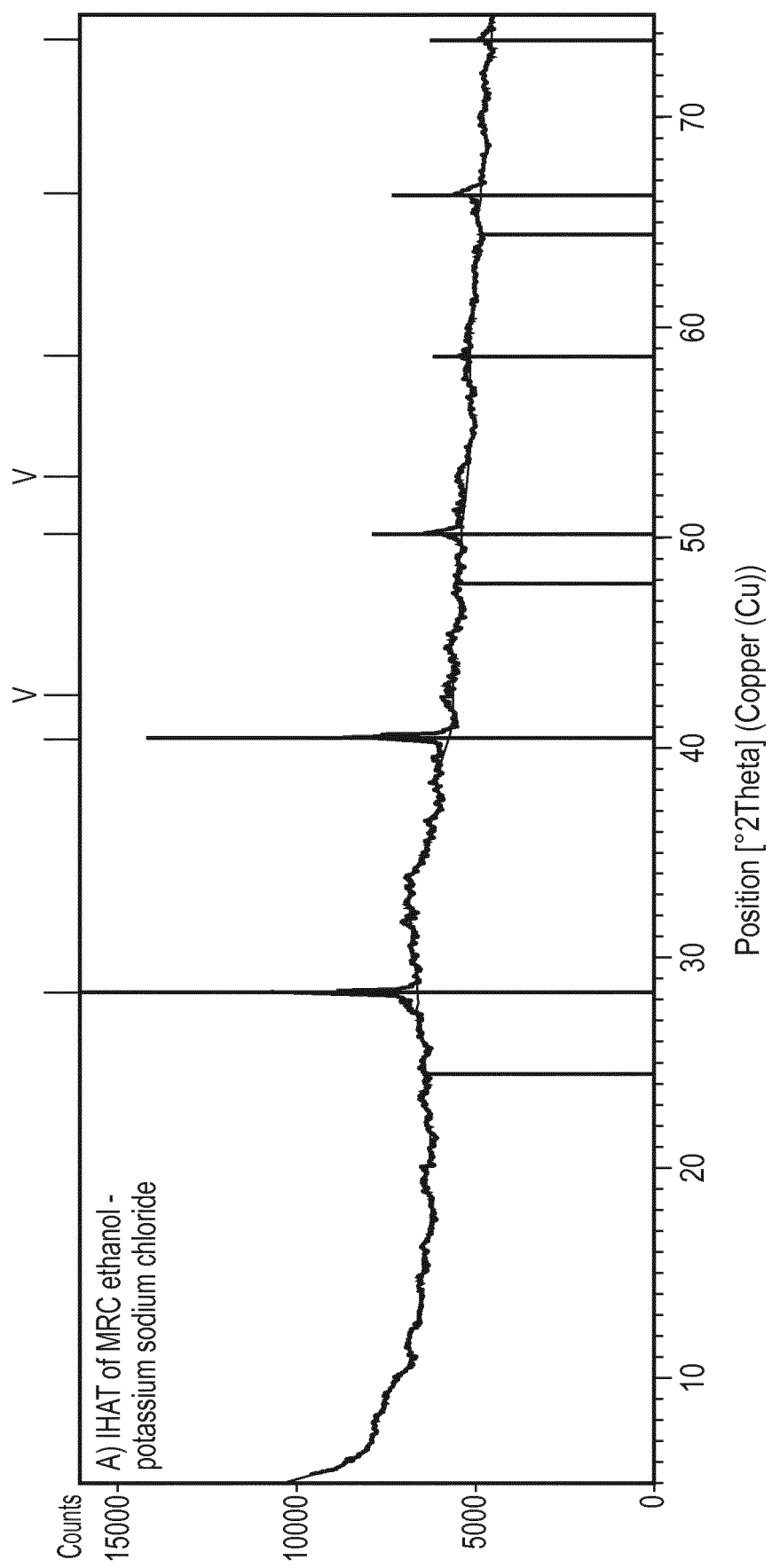
FIG. 4. X-ray diffractogram of an IHAT powder produced after ethanolic recovery (as per Example 4) showing reduction, but not elimination, of NaCl and KCl traces relative to regular IHAT (shown in FIG. 2). Key NaCl and KCl peaks are indicated by vertical lines starting at the x axis.
Figure 5:
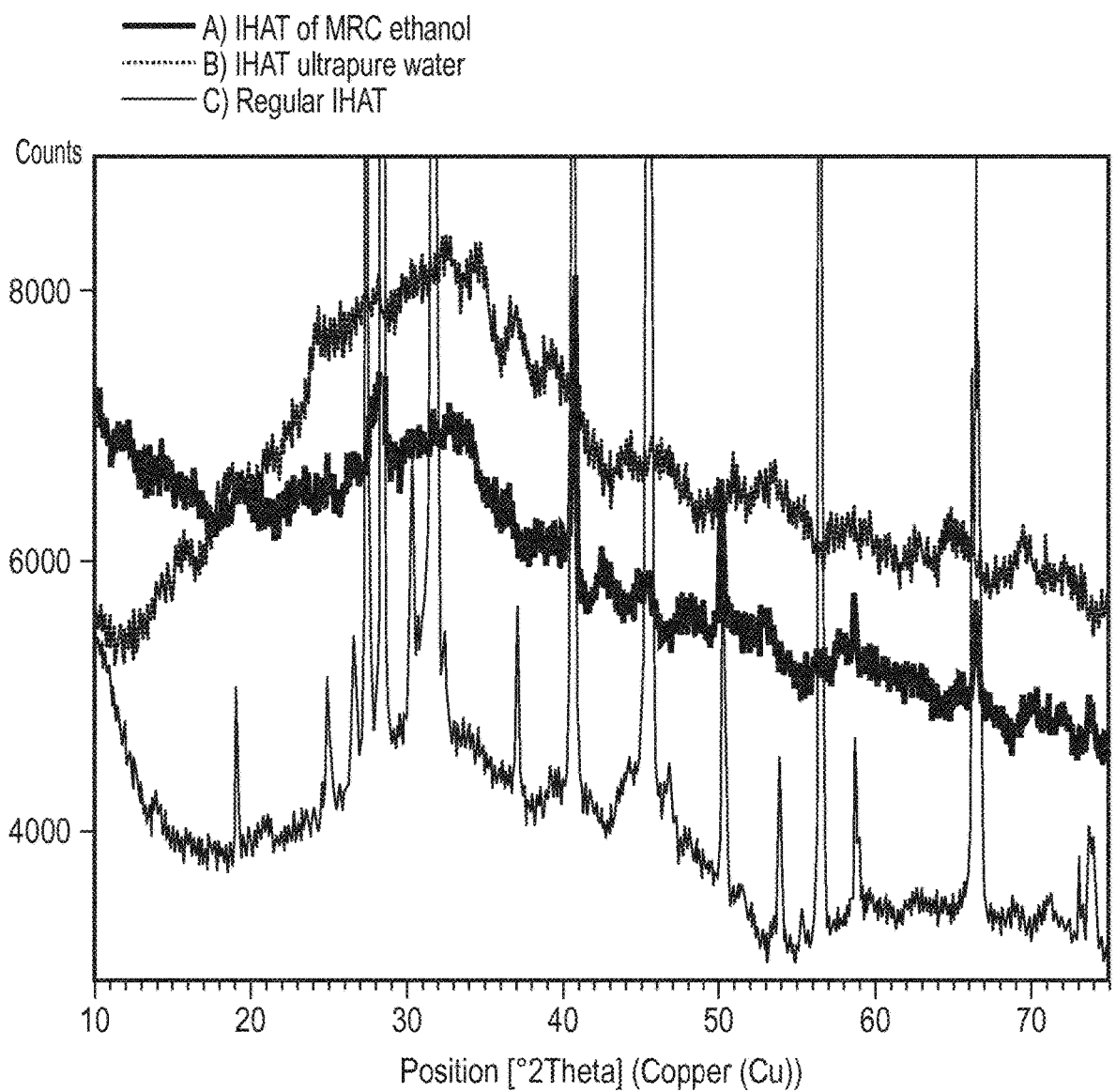
FIG. 5. Overlay of ferrihydrite XRD baselines for ultra-filtered (top), ethanolic recovered (middle) and regular (bottom) IHAT powders. Whilst all three spectra show a level of ferrihydrite disruption, ethanolic recovery resulted in additional disruption and reduction of crystallite size, as demonstrated by the attenuation of the ferrihydrite peak.
Figure 6:
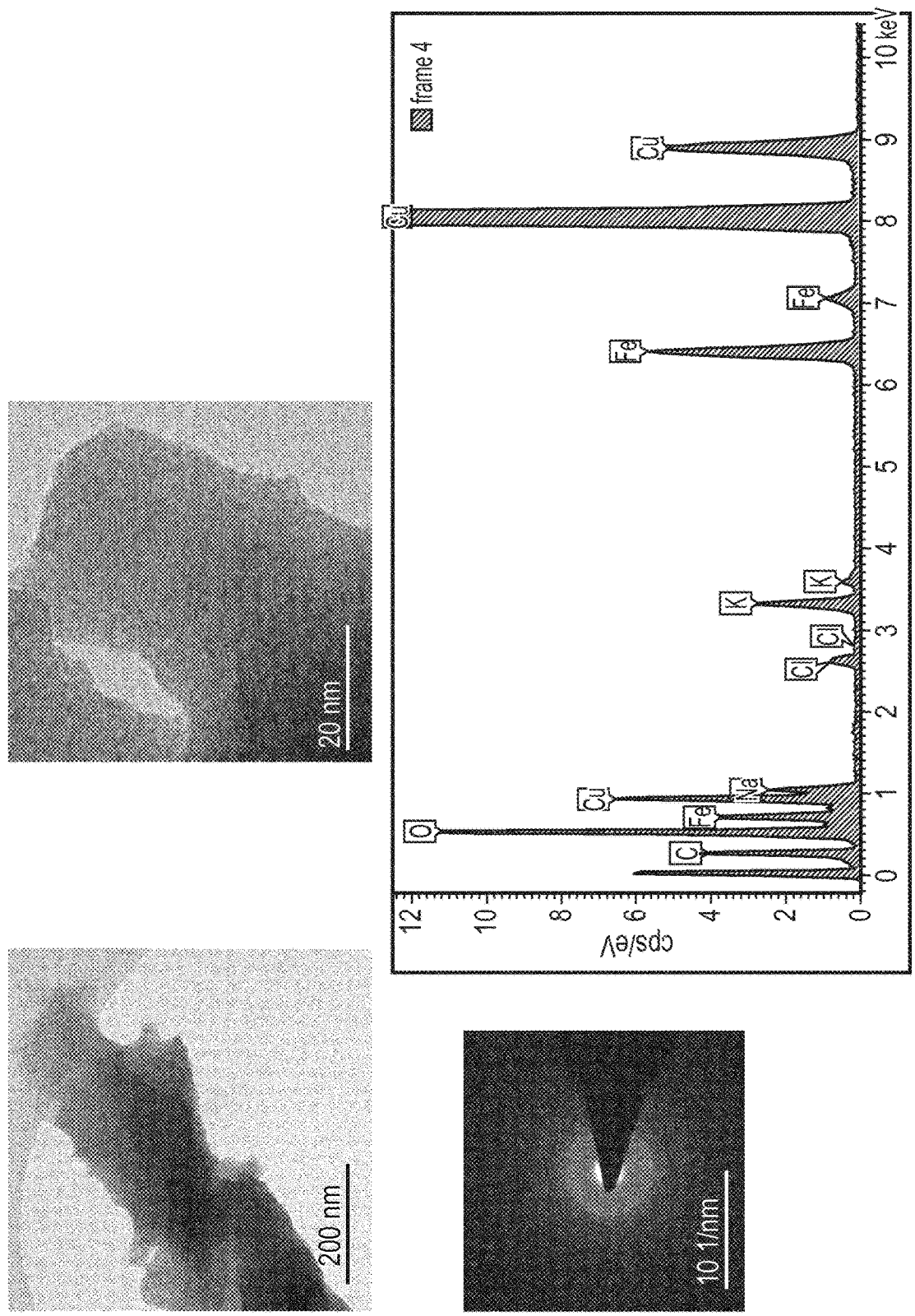
FIG. 6. Bright field analysis (top, right and left), diffraction pattern (bottom left) and spot EDX (bottom right) of ethanolic recovered IHAT (as per Example 4). Bright field analysis shows agglomerates of very fine-grained nanocrystalline material giving two broad selected area electron diffraction rings centred around 0.29 and 0.15 nm consistent with the main broad peak identified by XRD. The corresponding EDX spectrum shows Fe, O plus C, Na, K and Cl. Overall, these findings are consistent with a ligand-modified ferrihydrite.
Figure 7:
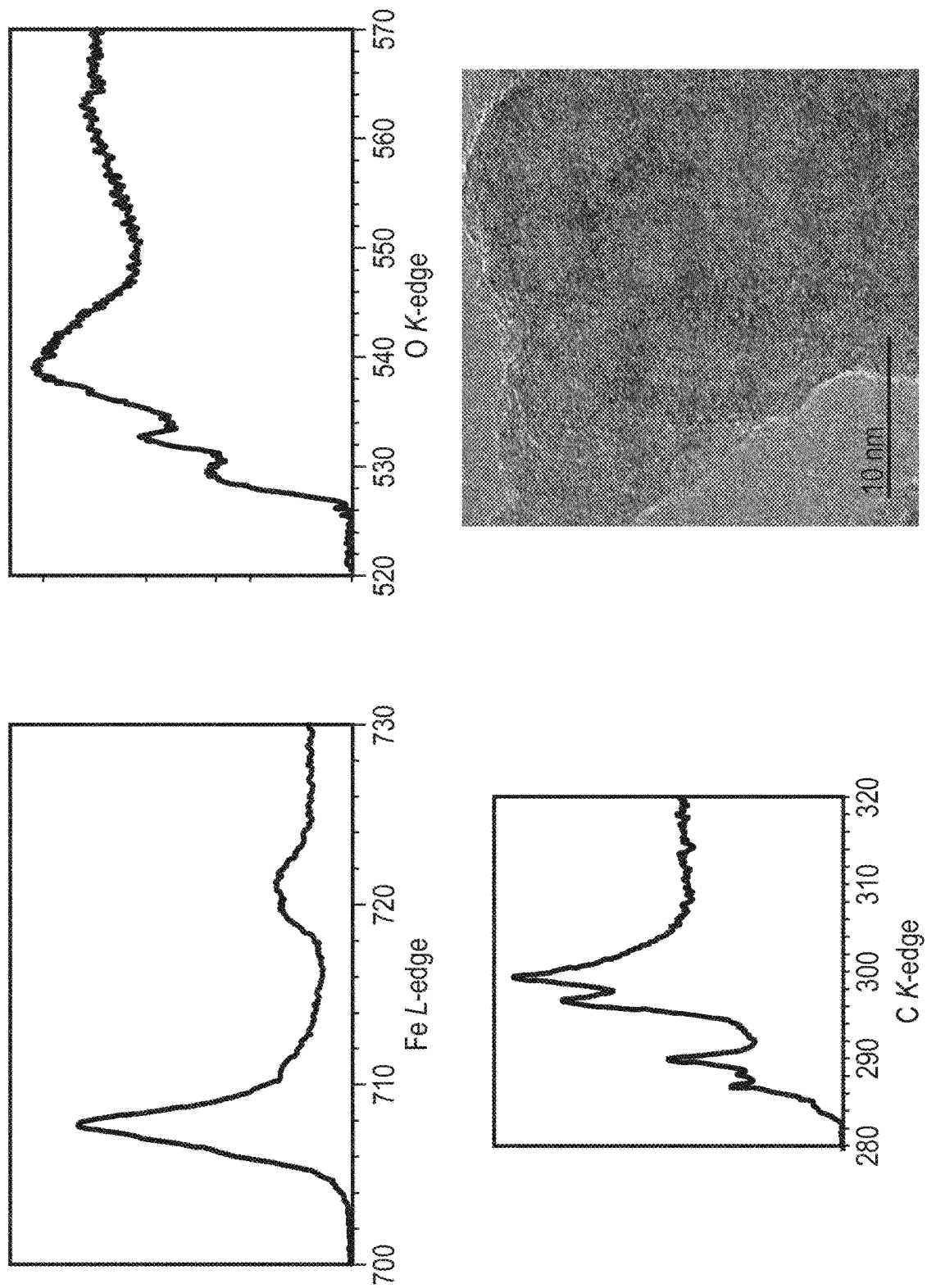
FIG. 7. Fe, O and C EELS edges (x-axis is in eV) of area shown in FIG. 6 and TEM image (bottom right) of the beam altered specimen after EEL analysis. EEL spectra are consistent with prior ligand modified ferrihydrite spectra for material collected by oven drying (ferric iron plus organic ligand-altered carbon and oxygen edges, see Pereira et al., Nanomedicine, 10(8): 1877-1886, 2014) and the TEM image recorded after the prolonged exposure required to collect EEL spectra confirms the nanocrystalline nature of the specimen upon beam damage (again as previously seen for material collected by oven drying; Pereira et al., Nanomedicine, 10(8): 1877-1886, 2014)
Figure 8:
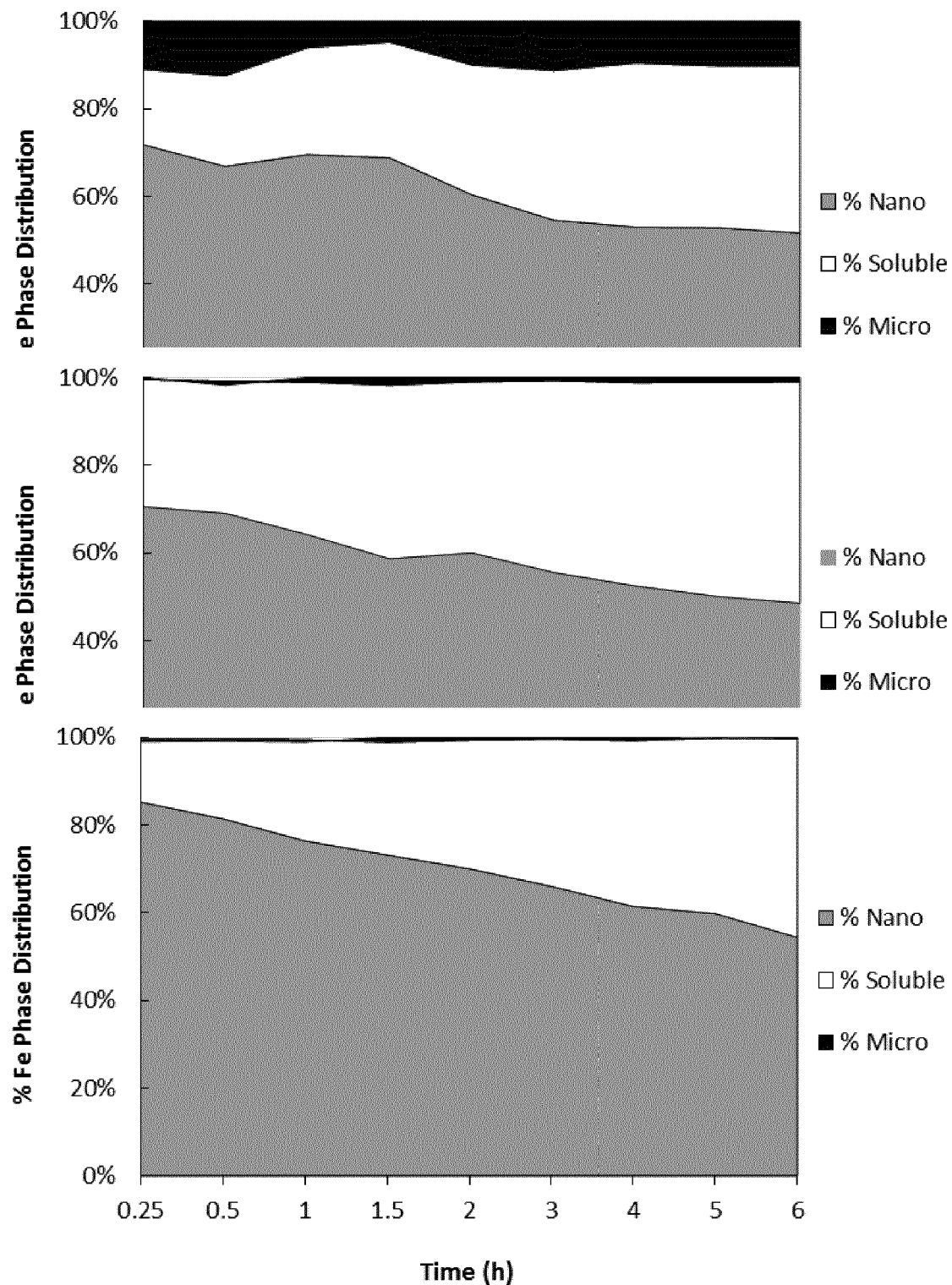
FIG. 8. In vitro lysosomal dissolution over time of regular (top), ethanolic recovered (middle) and ultra-filtered (bottom) IHAT materials.

In contrast, the ethanolic-recovery process disclosed herein is a fast and cheap process that also reduces the level of the unbound species present in the materials (FIG. 4) and increases their iron content (Table 1). Critically, despite the reduction in the carboxylate load, the mineral phase (i.e. ferrihydrite) of ethanolic-recovered materials remains disrupted (FIGS. 5 to 7) and crystallites are very small (FIG. 14). Mineral disruption leads to an increase in the chemical lability of iron oxo-hydroxide materials which is linked to their ability to release bioavailable iron. As such, adequate disruption of the mineral phase of ethanolic recovered IHAT was further confirmed through an in vitro lysosomal dissolution assay. This showed that dissolution rates of oven-dry, ultra-filtered and ethanolic-recovered IHAT materials have similar properties although the materials of the present invention dissolve more rapidly than the corresponding oven-dried ones (FIG. 8), attributed to their even smaller primary crystallite size.

TABLE 1

Iron content (as determined by ICP-OES) of IHAT materials recovered through different strategies.

| Material | % Fe (w/w) |
| --- | --- |
| Regular IHAT (Example 2) | 7.45 ± 0.1 |
| Ultrafiltered IHAT (Example 3) | 37.64 ± 0.01 |
| Ethanolic recovery IHAT (Example 4) | 26.5 ± 0.1 |

Figure 9:
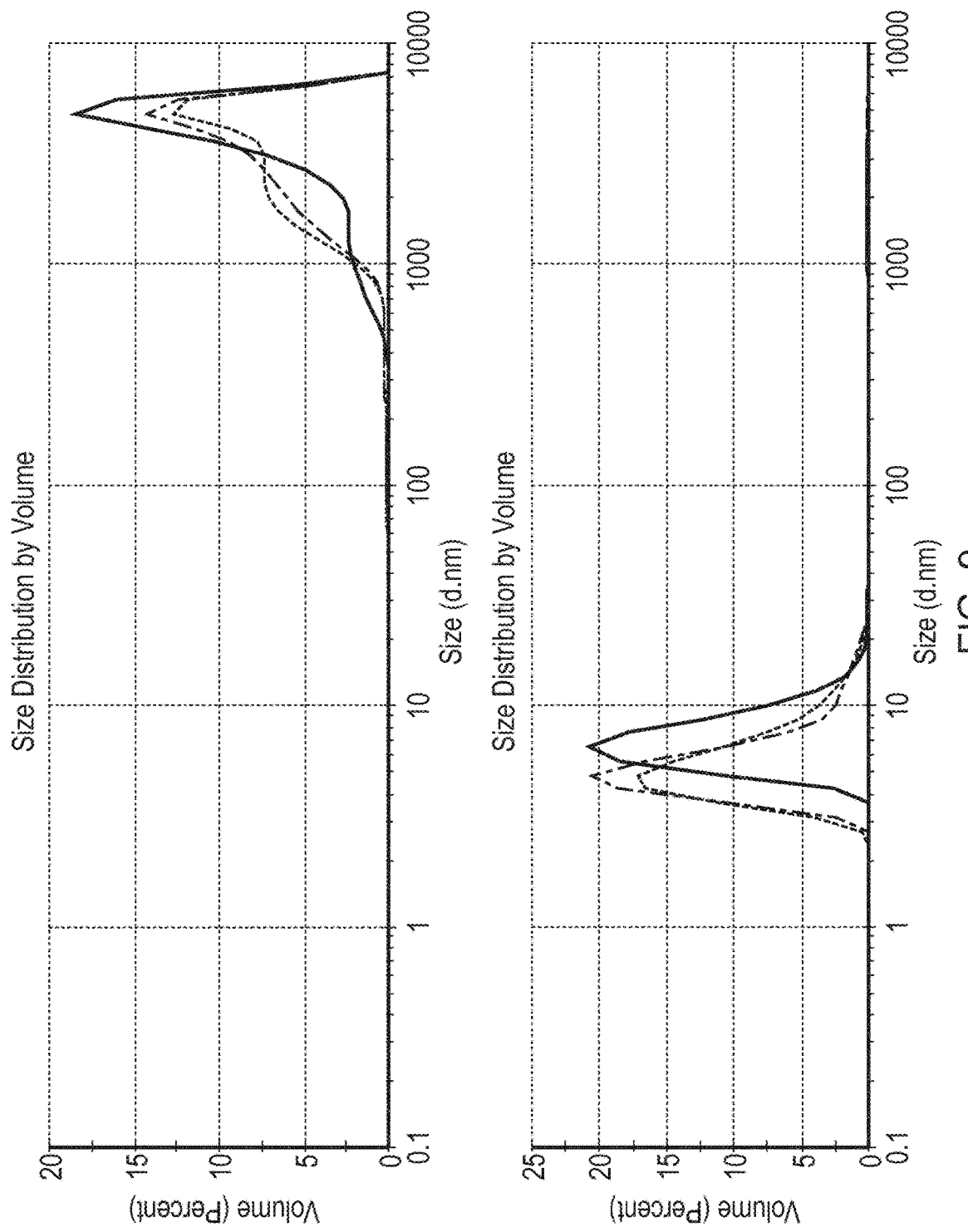
FIG. 9. Size distribution of IHAT re-suspended in water to original concentration after oven drying (as per Example 2) showing presence of agglomerates (top). Removal of aggregates by centrifugation enables size determination of the colloidal fraction (bottom).
Figure 10:
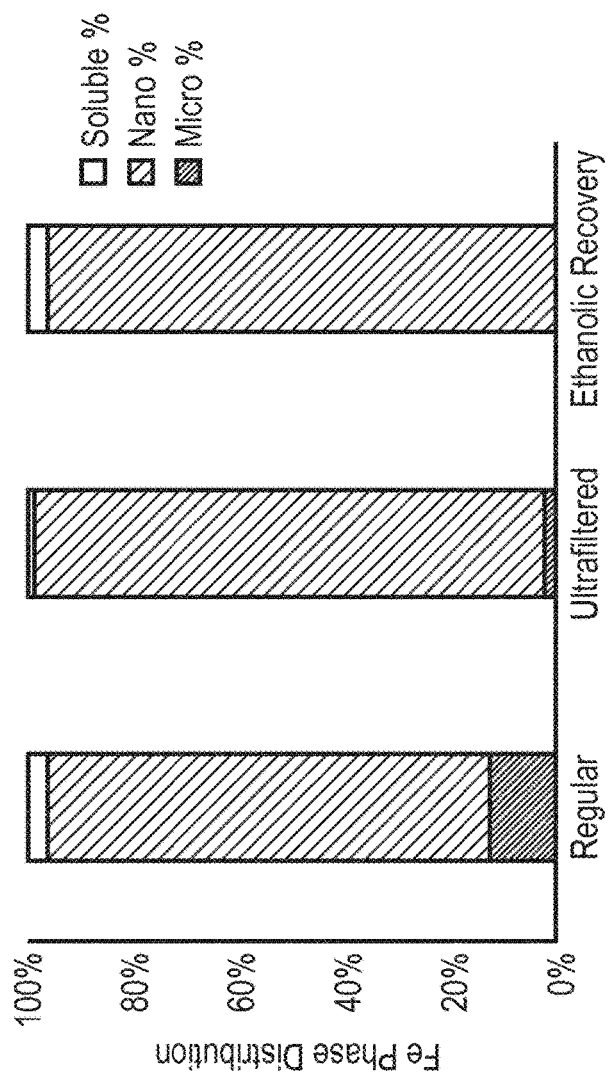
FIG. 10. Phase distribution after resuspending ultra-filtered, ethanolic recovered or oven dried (i.e. regular) IHAT to their original iron concentrations. The three dry materials were produced from the same IHAT suspension (40 mM Fe; pH 7.42).
Figure 11:
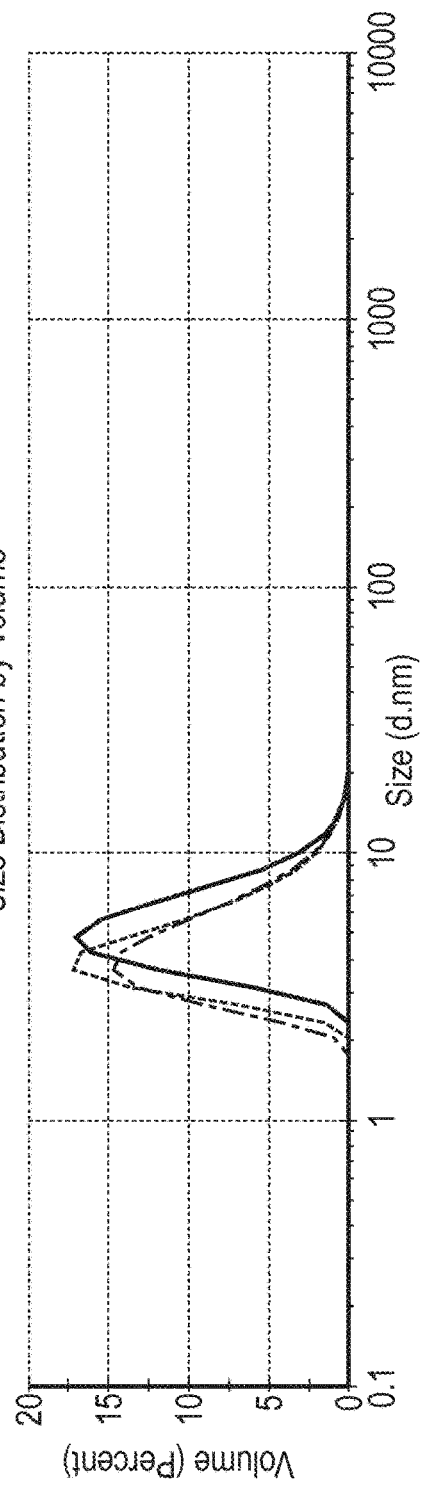
FIG. 11. Size distribution of ethanolic recovered IHAT (example 4) that was re-suspended in water to its original concentration (40 mM). Note that upon resuspension agglomerates were absent, unlike in FIG. 8. Each individual trace corresponds to an analytical replicate (N=3).

The long drying times of the existing oven drying process (Example 2) also leads to the formation of an unwanted fraction of irreversible aggregates that do not resuspend when back in water (FIG. 9) and which are therefore not a source of bioavailable iron. In contrast, when re-hydrated, ethanolic-recovery materials re-suspend completely (FIG. 10) to their original size (FIG. 11). This is highly surprising since the carboxylate load, which contributes to the stability of these suspensions through electrostatic repulsion, is greatly reduced with the ethanolic-recovery process and in the art would normally be anticipated as essential to disperse the particles. Therefore the method produces materials with several advantages over prior art IHAT materials: overall it produces even smaller primary particle sizes of the carboxylate ligand modified ferric iron oxo-hydroxides which are more easily dissolved under lysosomal conditions and thus expected to be more bioavailable; it prevents aggregation and/or agglomeration of a fraction of the dried material; and the reduction in the carboxylate content of the materials increases the overall iron content present in the materials on a percentage weight for weight basis.

Figure 12:
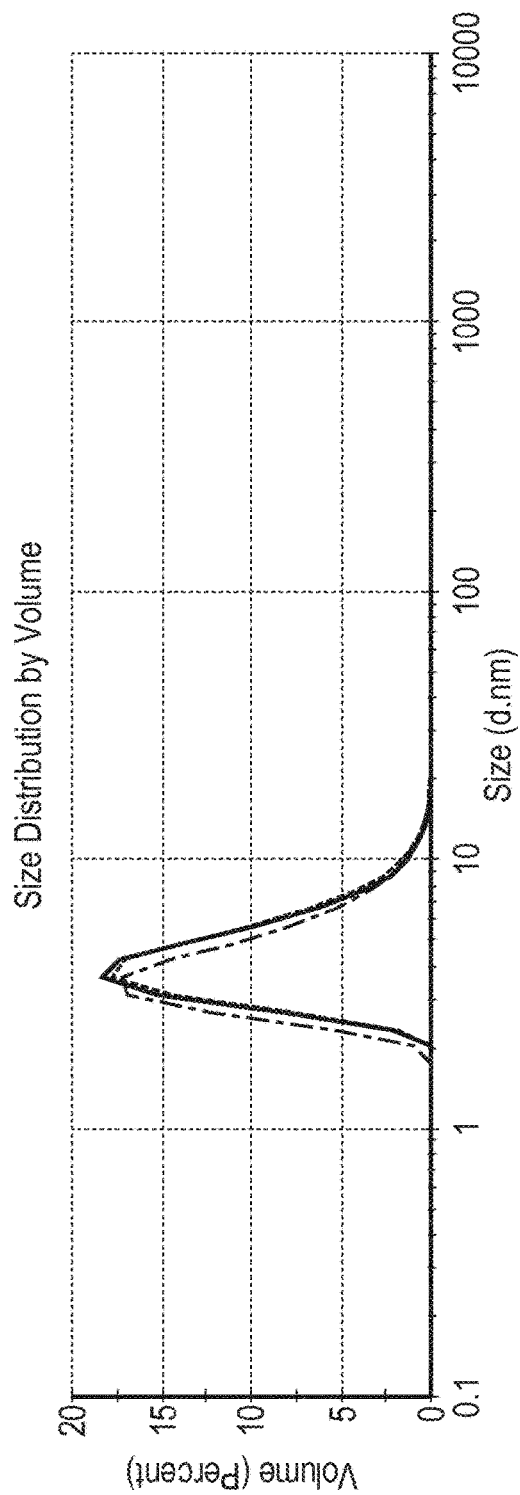
FIG. 12. Size distribution (mean $DV_{0.5}$=4.0 nm) of acetonic recovered IHAT (Example 6) re-suspended in water back to 40 mM Fe. Each individual trace corresponds to an analytical replicate (N=3).
Figure 13:
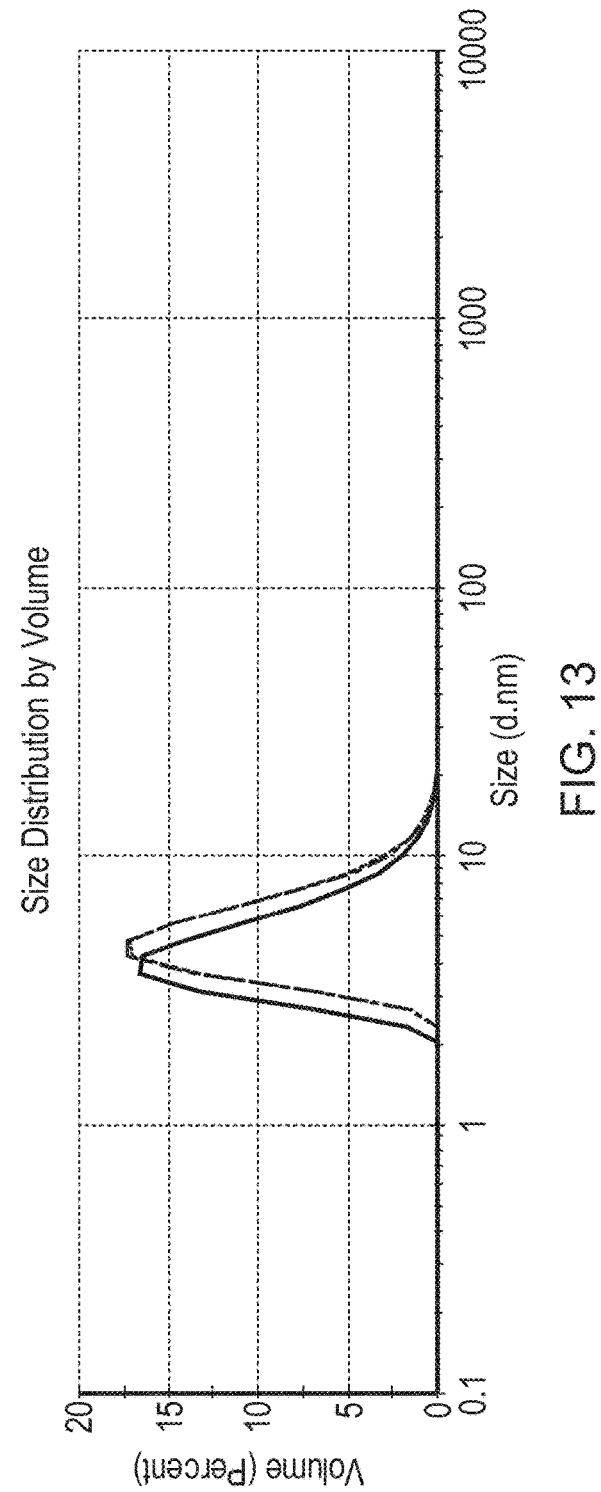
FIG. 13. Size distribution (mean $DV_{0.5}$=4.8 nm) of methanolic recovered IHAT (Example 5) re-suspended in water back to 40 mM Fe. Each individual trace corresponds to an analytical replicate (N=3).

The experiments described above also show that other water miscible non-aqueous solvents, in particular acetone (FIG. 12) and methanol (FIG. 13), can be utilised instead of ethanol.

Carboxylate Content in Ethanolically Recovered IHAT

Prior to ethanolic synthesis, IHAT (as per Example 1) comprised a ligand:iron ratio of 0.5:1 for both adipate and tartrate. Analysis of the carboxylate content of ethanolic recovered material (produced as per Example 4) showed that the tartrate:iron ratio had only dropped to 0.40:1 whereas the adipate:iron ratio had dropped to 0.09:1. Whilst not wishing to be bound by any particular theory, the carboxylate content in ethanolically recovered IHAT may be indicative of a greater level of association and/or modification to the oxo-hydroxide mineral by tartrate than by the adipate.

REFERENCES

The following references are expressly incorporated by reference for all purposes in their entirety.

Pereira et al., Nanomedicine, 10(8): 1877-1886, 2014. doi: 10.1016/j.nano.2014.06.012

Aslam et al., Ferroportin mediates the intestinal absorption of iron from a nanoparticulate ferritin core mimetic in mice. FASEB J. 28(8):3671-3678, 2014.

Powell et al., A nano-disperse ferritin-core mimetic that efficiently corrects anaemia without luminal iron redox activity. Nanomedicine, 10(7):1529-1538, 2014.

WO 2008/096130.

http://www.rsc.org/chemistryworld/2014/12/solving-iron-solubility-problem-profile-mrc Heinrich. Bioavailability of trivalent iron in oral preparations. Arzeinmittelforshung/Drug Research 1975; 25(3): 420-426.

Geisser & Müller, Pharmacokinetics of iron salts and ferric hydroxide-carbohydrate complexes. Arzneimittelforshung/Drug Research, 37 (1): 100-104, 1987.

Nielsen et al., Bioavailability of iron from oral ferric polymaltose in humans. Arzneimittelforshung/Drug Research, 44(1): 743-748, 1994.

U.S. Pat. No. 3,076,798.

US 2006/0205691.

WO 2003/092674.

WO 2006/037449.

Harvey et al., Ferric trimaltol corrects iron deficiency anaemia in patients intolerant to iron. Alimentary Pharmacology & Therapeutics, 12(9):845-848, 1998.

WO 2003/097627.

WO 2004/074444.

US 2008/0274210.

Bobtelsky M and Jordan J. The structure and behaviour of ferric tartrate and citrate complexes in dilute solutions. J.A.C.S., 69: 2286-2290, 1947.
U.S. Pat. No. 3,821,192.
WO 2005/094203.
WO 2005/000210.
US 2005/0256,328.

The invention claimed is:

1. A composition comprising a carboxylate ligand modified ferric iron hydroxide material having a three dimensional polymeric structure in which the carboxylate ligands are non-stoichiometrically substituted for the oxo or hydroxy groups of the ferric iron hydroxide so that some of the ligand integrates into the solid phase by formal metal-ligand bonding,
wherein the three dimensional polymeric structure of the carboxylate ligand modified ferric iron hydroxide is such that the substitution of the oxo or hydroxy groups by the carboxylate ligands is random,
and
wherein the carboxylate ligand modified ferric iron hydroxide material is produced by a method comprising:
(i) mixing a colloidal suspension of the carboxylate ligand modified ferric iron hydroxide in a water miscible non-aqueous solvent to cause the carboxylate ligand modified ferric iron hydroxide to agglomerate;
(ii) recovering the agglomerated carboxylate ligand modified ferric iron hydroxide; and
(iii) drying the carboxylate ligand modified ferric iron hydroxide to produce the carboxylate ligand modified ferric iron hydroxide material;
wherein the carboxylate ligand comprises one or more dicarboxylate ligands of the formula HOOC—$R_1$—COOH or an ionised form thereof, wherein $R_1$ is an optionally substituted $C_{1-10}$ alkyl, $C_{1-10}$ alkenyl or $C_{1-10}$ alkynyl group; and
wherein the water miscible non-aqueous solvent is selected from ethanol, methanol and/or acetone.

2. The composition of claim 1, wherein the carboxylate ligand modified ferric iron hydroxide material comprises adipate and tartrate ligands or tartrate and succinate ligands or succinate and adipate ligands.

3. The composition of claim 2, wherein the ligands and ferric iron ions are present in a molar ratio of 1:1:2 (tartrate:adipate:Fe), 1:1:2 (tartrate:succinate:Fe), 1:6:2 (tartrate:succinate:Fe) or 1:1:2 (succinate:adipate:Fe).

4. The composition of claim 1, wherein the carboxylate ligand modified ferric iron hydroxide material comprises tartrate/tartaric acid ligands.

5. The composition of claim 1, wherein the carboxylate ligand modified ferric iron hydroxide has an iron content of at least 10% Fe (w/w), or at least 20% Fe (w/w).

6. An iron supplement tablet, capsule or powder comprising the composition of claim 1.

7. A method for treating iron deficiency anaemia, iron deficiency and anaemia of chronic disease in a patient, the method comprising administering to the patient a therapeutically effective amount of the composition of claim 1.

8. The method of claim 7, wherein the composition is administered orally.

9. The composition of claim 1, wherein the method further comprises initial steps of mixing a solution of ferric iron ions and one or more carboxylic acid ligands or carboxylate ligands and increasing the pH of the solution to cause formation of the colloidal suspension of the carboxylate ligand modified ferric iron hydroxide.

10. The composition of claim 9, wherein the pH is increased by the addition of alkali, optionally wherein the alkali is sodium hydroxide.

11. The composition of claim 9, wherein the pH is increased to a pH between 7.0 and 9.0.

12. The composition of claim 9, wherein the pH is increased to a pH between 7.4 and 8.5.

13. The composition of claim 2, wherein the carboxylate ligand modified ferric iron hydroxide in the colloidal suspension comprises a concentration of ferric iron between 20 mM and 1000 mM, a concentration of adipate between 10 mM and 150 mM, and a concentration of tartrate between 10 mM and 500 mM.

14. The composition of claim 13, wherein the carboxylate ligand modified ferric iron hydroxide in the colloidal suspension comprises a concentration of ferric iron between 20 mM and 80 mM, a concentration of adipate between 10 mM and 40 mM, and a concentration of tartrate between 10 mM and 40 mM.

15. The composition of claim 13, wherein the carboxylate ligand modified ferric iron hydroxide in the colloidal suspension comprises a concentration of ferric iron of about 40 mM, a concentration of adipate of about 20 mM, and a concentration of tartrate of about 20 mM.

16. The composition of claim 13, wherein the carboxylate ligand modified ferric iron hydroxide in the colloidal suspension comprises a concentration of ferric iron of about 200 mM, a concentration of adipate of about 100 mM, and a concentration of tartrate of about 100 mM.

17. The composition of claim 1, wherein the carboxylate ligand modified ferric iron hydroxide material comprises tartrate and/or tartaric acid ligands.

18. The composition of claim 1, wherein the ratio of the volume of the water miscible non-aqueous solvent to the colloidal suspension of the carboxylate ligand modified ferric iron hydroxide is between 1:1 and 5:1.

19. The composition of claim 1, wherein the water miscible non-aqueous solvent is ethanol.

20. The composition of claim 1, wherein the drying step takes 24 hours or less at 45° C.

21. The composition of claim 1, wherein the steps of agglomerating the suspension and recovering the agglomerated carboxylate ligand modified ferric iron hydroxide removes unreacted ferric iron ions (Fe3+), sodium chloride and/or one or more carboxylic acid ligands or carboxylate ligands from the carboxylate ligand modified ferric iron hydroxide.

22. The composition of claim 1, where the carboxylate ligand modified ferric iron hydroxide material has a mean particle size between 1 and 10 nm.

23. The composition of claim 1, wherein the metal-ligand bonding disrupts the structure of the carboxylate ligand modified ferric iron hydroxide material as determined using X-ray diffraction (XRD).

24. The composition of claim 23, wherein the carboxylate ligand modified ferric iron hydroxide material has a structure that is consistent with ligand modified ferrihydrite collected by oven drying, wherein the structure is determined by electron energy-loss spectroscopy (EELS), and wherein the EELS spectrum comprises ferric iron and organic ligand-altered carbon and oxygen edges.

25. The composition of claim 1, wherein the method further comprises a step of milling or micronizing the carboxylate ligand modified ferric iron hydroxide material.

26. The composition of claim 1, wherein the method further comprises a step of formulating the carboxylate ligand modified ferric iron hydroxide material by mixing it with one or more pharmaceutically acceptable excipients.

27. The composition of claim 26, wherein the method further comprises making tablets or capsules.

28. The composition of claim 26, wherein the carboxylate ligand modified ferric iron hydroxide material is formulated for oral delivery.

29. The composition of claim 1, wherein the optional substitution comprises one or more hydroxyl groups.

30. A composition comprising a carboxylate ligand modified ferric iron hydroxide material having a three dimensional polymeric structure in which the carboxylate ligands are non-stoichiometrically substituted for the oxo or hydroxy groups of the ferric iron hydroxide so that some of the ligand integrates into the solid phase by formal metal-ligand bonding, wherein the three dimensional polymeric structure of the carboxylate ligand modified ferric iron hydroxide is such that the substitution of the oxo or hydroxy groups by the carboxylate ligands is random, and wherein the carboxylate ligand modified ferric iron hydroxide material is produced by a method comprising:

(i) mixing a colloidal suspension of the carboxylate ligand modified ferric iron hydroxide in a water miscible non-aqueous solvent to cause the carboxylate ligand modified ferric iron hydroxide to agglomerate;

(ii) recovering the agglomerated carboxylate ligand modified ferric iron hydroxide; and (iii) drying the carboxylate ligand modified ferric iron hydroxide to produce the carboxylate ligand modified ferric iron hydroxide material;

wherein the carboxylate ligand comprises one or more dicarboxylate ligands of the formula $HOOC-R_1-COOH$ or an ionised form thereof, wherein $R_1$ is an optionally substituted $C_{1-10}$ alkyl, $C_{1-10}$ alkenyl or $C_{1-10}$ alkynyl group; and wherein the water miscible non-aqueous solvent is selected from ethanol, methanol and/or acetone; and wherein on dispersion in water the composition produces a microparticulate ferric iron fraction comprising less than 3.0% of the total ferric iron present in the composition when dispersed in water at a concentration of 40 mM Fe, and the microparticulate ferric iron fraction produced upon dispersion in water is free of aggregates of the carboxylate ligand modified ferric iron hydroxide material.

\* \* \* \* \*